(12) United States Patent
Nikolchev et al.

(10) Patent No.: US 8,733,361 B2
(45) Date of Patent: May 27, 2014

(54) OCCLUSION DEVICES AND METHODS

(71) Applicant: Conceptus, Inc., Mountain View, CA (US)

(72) Inventors: Julian N. Nikolchev, Portola Valley, CA (US); Dai T. Ton, Milpitas, CA (US); Ashish Khera, Maplewood, NJ (US); Donnell W. Gurskis, Belmont, CA (US); Steven Bacich, Half Moon Bay, CA (US)

(73) Assignee: Bayer Essure Inc., Milpitas, CA (US)

( * ) Notice: Subject to any disclaimer, the term of this patent is extended or adjusted under 35 U.S.C. 154(b) by 0 days.

(21) Appl. No.: 13/680,469

(22) Filed: Nov. 19, 2012

(65) Prior Publication Data

US 2013/0139827 A1   Jun. 6, 2013

Related U.S. Application Data

(63) Continuation of application No. 13/294,758, filed on Nov. 11, 2011, now Pat. No. 8,327,852, which is a continuation of application No. 12/908,756, filed on Oct. 20, 2010, now Pat. No. 8,171,936, which is a continuation of application No. 10/600,298, filed on Jun. 20, 2003, now abandoned, which is a continuation-in-part of application No. 09/093,835, filed on Jun. 8, 1998, now Pat. No. 6,705,323, which is a continuation-in-part of application No. 08/475,252, filed on Jun. 7, 1995, now abandoned, and a continuation-in-part of application No. 08/474,779, filed on Jun. 7, 1995, now Pat. No. 6,176,240.

(60) Provisional application No. 60/059,861, filed on Sep. 24, 1997.

(51) Int. Cl.
*A61F 6/06* (2006.01)

(52) U.S. Cl.
USPC ............................ 128/830; 128/831

(58) Field of Classification Search
USPC ................... 128/830–841; 606/108, 191, 198
See application file for complete search history.

(56) References Cited

U.S. PATENT DOCUMENTS

| 2,102,270 | A | 12/1937 | Mortimer |
| 2,365,296 | A | 12/1944 | Schimpf |

(Continued)

FOREIGN PATENT DOCUMENTS

| AU | 32520/78 | 7/1979 |
| CN | 1047447 | 5/1990 |

(Continued)

OTHER PUBLICATIONS

Brueschke, et al., "A Steerable Hysteroscopic and Mechanical Tubal Occlusive Devices", *Advances in Female Sterilization Techniques*, Eds., Harper & Row, Publishers, 1976, pp. 182-198.

(Continued)

*Primary Examiner* — Michael A. Brown
(74) *Attorney, Agent, or Firm* — Blakely, Sokoloff, Taylor & Zafman LLP

(57) ABSTRACT

The invention provides intrafallopian devices and non-surgical methods for their placement to prevent conception. The efficacy of the device is enhanced by forming the structure at least in part from copper or copper alloy. The device is anchored within the fallopian tube by a lumen-traversing region of the resilient structure which has helical outer surface, together with a portion of the resilient structure which is biased to form a bent secondary shape, the secondary shape having a larger cross-section than the fallopian tube. The resilient structure is restrained in a straight configuration and transcervically inserted within the fallopian tube, where it is released. Optionally, permanent sterilization is effected by passing a current through the resilient structure to the tubal walls.

1 Claim, 15 Drawing Sheets

(56) References Cited

U.S. PATENT DOCUMENTS

| | | | |
|---|---|---|---|
| 3,042,030 | A | 7/1962 | Read |
| 3,334,629 | A | 8/1967 | Cohn |
| 3,404,682 | A | 10/1968 | Waldron |
| 3,405,711 | A | 10/1968 | Bakunin |
| 3,422,813 | A | 1/1969 | Braley, Jr. et al. |
| 3,463,141 | A | 8/1969 | Mozolf |
| 3,467,090 | A | 9/1969 | Zollett |
| 3,561,438 | A | 2/1971 | Canel |
| 3,563,235 | A | 2/1971 | Zipper |
| 3,598,115 | A | 8/1971 | Horne, Jr. |
| 3,620,212 | A | 11/1971 | Fannon et al. |
| 3,675,639 | A | 7/1972 | Cimber |
| 3,675,642 | A | 7/1972 | Lord |
| 3,680,542 | A | 8/1972 | Cimber |
| 3,687,129 | A | 8/1972 | Nuwayser |
| 3,722,500 | A | 3/1973 | Robinson |
| 3,760,806 | A | 9/1973 | Leeper |
| 3,763,856 | A | 10/1973 | Blomberg |
| 3,768,102 | A | 10/1973 | Kwan-Gett et al. |
| 3,774,600 | A | 11/1973 | Cognat |
| 3,803,308 | A | 4/1974 | Zipper |
| 3,805,767 | A | 4/1974 | Erb |
| 3,840,016 | A | 10/1974 | Lindemann |
| 3,858,571 | A | 1/1975 | Rudolph |
| 3,858,586 | A | 1/1975 | Lessen |
| 3,868,956 | A | 3/1975 | Alfidi et al. |
| 3,895,634 | A | 7/1975 | Berger et al. |
| 3,918,431 | A | 11/1975 | Sinnreich |
| 3,926,195 | A | 12/1975 | Bleier et al. |
| 3,938,527 | A | 2/1976 | Rioux et al. |
| 3,973,560 | A | 8/1976 | Emmett |
| 3,982,542 | A | 9/1976 | Ford et al. |
| 4,003,380 | A | 1/1977 | Wien |
| RE29,345 | E | 8/1977 | Erb |
| 4,040,417 | A | 8/1977 | Zipper |
| 4,057,063 | A | 11/1977 | Gieles et al. |
| 4,085,743 | A | 4/1978 | Yoon |
| 4,111,196 | A | 9/1978 | Emmett |
| 4,135,495 | A | 1/1979 | Borgen |
| 4,136,695 | A | 1/1979 | Dafoe |
| 4,140,126 | A | 2/1979 | Choudhury |
| 4,143,656 | A | 3/1979 | Holmes |
| 4,158,050 | A | 6/1979 | Zipper |
| 4,160,446 | A | 7/1979 | Barrington |
| 4,181,725 | A | 1/1980 | Voorhees et al. |
| 4,185,618 | A | 1/1980 | Corey |
| 4,207,891 | A | 6/1980 | Boldue |
| 4,245,623 | A | 1/1981 | Erb |
| 4,246,896 | A | 1/1981 | Horne, Jr. et al. |
| 4,326,511 | A | 4/1982 | Zimerman |
| 4,353,363 | A | 10/1982 | Sopena Quesada |
| 4,365,621 | A | 12/1982 | Brundin |
| 4,374,523 | A | 2/1983 | Yoon |
| 4,416,660 | A | 11/1983 | Dafoe |
| 4,478,837 | A | 10/1984 | Schenker |
| 4,485,814 | A | 12/1984 | Yoon |
| 4,503,569 | A | 3/1985 | Dotter |
| 4,509,504 | A | 4/1985 | Brundin |
| 4,523,590 | A | 6/1985 | Roth et al. |
| 4,537,186 | A | 8/1985 | Verschoof et al. |
| 4,572,162 | A | 2/1986 | Livesay et al. |
| 4,574,806 | A | 3/1986 | McCarthy |
| 4,579,110 | A | 4/1986 | Hamou |
| 4,595,000 | A | 6/1986 | Hamou |
| 4,601,698 | A | 7/1986 | Moulding, Jr. |
| 4,606,336 | A | 8/1986 | Zeluff |
| 4,612,924 | A | 9/1986 | Cimber |
| 4,628,924 | A | 12/1986 | Cimber |
| 4,638,803 | A | 1/1987 | Rand |
| 4,655,771 | A | 4/1987 | Wallsten |
| 4,700,701 | A | 10/1987 | Montaldi |
| 4,715,365 | A | 12/1987 | Cimber |
| 4,717,387 | A | 1/1988 | Inoue et al. |
| 4,724,832 | A | 2/1988 | Strubel et al. |
| 4,727,866 | A | 3/1988 | Livesay et al. |
| 4,731,052 | A | 3/1988 | Seitz, Jr. |
| 4,733,665 | A | 3/1988 | Palmaz |
| 4,788,966 | A | 12/1988 | Yoon |
| 4,805,618 | A | 2/1989 | Ueda et al. |
| 4,808,399 | A | 2/1989 | Rypacek et al. |
| 4,821,741 | A | 4/1989 | Mohajer |
| 4,824,434 | A | 4/1989 | Seitz, Jr. |
| 4,846,834 | A | 7/1989 | Von Recum et al. |
| 4,932,421 | A | 6/1990 | Kaali et al. |
| 4,932,422 | A | 6/1990 | Ragheb |
| 4,937,254 | A | 6/1990 | Sheffield et al. |
| 4,943,290 | A | 7/1990 | Rexroth et al. |
| 4,969,458 | A | 11/1990 | Wiktor |
| 4,970,298 | A | 11/1990 | Silver et al. |
| 4,983,177 | A | 1/1991 | Wolf |
| 4,994,069 | A | 2/1991 | Ritchart et al. |
| 5,002,552 | A | 3/1991 | Casey |
| 5,065,751 | A | 11/1991 | Wolf |
| 5,071,407 | A | 12/1991 | Termin et al. |
| 5,095,917 | A | 3/1992 | Vancaillie |
| 5,108,420 | A | 4/1992 | Marks |
| 5,122,136 | A | 6/1992 | Guglielmi et al. |
| 5,122,137 | A | 6/1992 | Lennox |
| 5,133,709 | A | 7/1992 | Prince |
| 5,147,353 | A | 9/1992 | Everett et al. |
| 5,147,370 | A | 9/1992 | McNamara et al. |
| 5,147,400 | A | 9/1992 | Kaplan et al. |
| 5,163,958 | A | 11/1992 | Pinchuk |
| 5,176,692 | A | 1/1993 | Wilk et al. |
| 5,192,301 | A | 3/1993 | Kamiya et al. |
| 5,195,964 | A | 3/1993 | Kletzky et al. |
| 5,197,978 | A | 3/1993 | Hess |
| 5,207,684 | A | 5/1993 | Nobles |
| 5,222,964 | A | 6/1993 | Cooper |
| 5,226,911 | A * | 7/1993 | Chee et al. .................... 606/191 |
| 5,234,437 | A | 8/1993 | Sepetka |
| 5,244,096 | A | 9/1993 | Stoner |
| 5,250,071 | A | 10/1993 | Palermo |
| 5,254,132 | A | 10/1993 | Barley et al. |
| 5,259,836 | A | 11/1993 | Thurmond et al. |
| 5,261,916 | A | 11/1993 | Engelson |
| 5,303,719 | A | 4/1994 | Wilk et al. |
| 5,304,194 | A | 4/1994 | Chee et al. |
| 5,304,195 | A | 4/1994 | Twyford, Jr. et al. |
| 5,304,228 | A | 4/1994 | Prince |
| 5,312,415 | A | 5/1994 | Palermo |
| 5,330,483 | A | 7/1994 | Heaven et al. |
| 5,342,348 | A | 8/1994 | Kaplan |
| 5,346,498 | A | 9/1994 | Greelis et al. |
| 5,350,397 | A | 9/1994 | Palermo et al. |
| 5,354,295 | A | 10/1994 | Guglielmi et al. |
| 5,354,309 | A | 10/1994 | Schnepp-Pesch et al. |
| 5,356,388 | A | 10/1994 | Sepetka et al. |
| 5,364,393 | A | 11/1994 | Auth et al. |
| 5,366,472 | A | 11/1994 | Hillstead |
| 5,377,668 | A | 1/1995 | Ehmsen et al. |
| 5,382,259 | A | 1/1995 | Phelps et al. |
| 5,382,260 | A | 1/1995 | Dormandy et al. |
| 5,382,261 | A | 1/1995 | Palmaz |
| 5,389,089 | A | 2/1995 | Bauer et al. |
| 5,389,100 | A | 2/1995 | Bacich et al. |
| 5,411,549 | A | 5/1995 | Peters |
| 5,423,829 | A | 6/1995 | Pham et al. |
| 5,423,849 | A | 6/1995 | Engelson et al. |
| 5,433,708 | A | 7/1995 | Nichols et al. |
| 5,443,500 | A | 8/1995 | Sigwart |
| 5,458,636 | A | 10/1995 | Brancato |
| 5,469,867 | A | 11/1995 | Schmitt |
| 5,474,089 | A | 12/1995 | Waynant |
| 5,499,995 | A | 3/1996 | Teirstein |
| 5,507,768 | A | 4/1996 | Lau et al. |
| 5,514,176 | A | 5/1996 | Bosley, Jr. |
| 5,522,822 | A | 6/1996 | Phelps et al. |
| 5,522,836 | A | 6/1996 | Palermo |
| 5,534,007 | A | 7/1996 | St. Germain et al. |
| 5,545,210 | A | 8/1996 | Hess et al. |
| 5,549,624 | A | 8/1996 | Mirigian et al. |
| 5,555,896 | A | 9/1996 | Cimber |
| 5,556,396 | A | 9/1996 | Cohen et al. |

(56) References Cited

U.S. PATENT DOCUMENTS

| | | | |
|---|---|---|---|
| 5,562,641 A | 10/1996 | Flomenblit et al. |
| 5,562,654 A | 10/1996 | Smith |
| 5,569,245 A | 10/1996 | Guglielmi et al. |
| 5,578,074 A | 11/1996 | Mirigian |
| 5,582,619 A * | 12/1996 | Ken ............................ 606/191 |
| 5,601,593 A | 2/1997 | Freitag |
| 5,601,600 A | 2/1997 | Ton |
| 5,624,449 A | 4/1997 | Pham et al. |
| 5,624,461 A | 4/1997 | Mariant |
| 5,630,797 A | 5/1997 | Diedrich et al. |
| 5,634,877 A | 6/1997 | Salama |
| 5,639,277 A | 6/1997 | Mariant et al. |
| 5,649,949 A | 7/1997 | Wallace et al. |
| 5,656,036 A | 8/1997 | Palmaz |
| 5,662,712 A | 9/1997 | Pathak et al. |
| 5,669,931 A | 9/1997 | Kupiecki et al. |
| 5,690,666 A | 11/1997 | Berenstein et al. |
| 5,690,842 A | 11/1997 | Panchinson |
| 5,718,711 A | 2/1998 | Berenstein et al. |
| 5,725,777 A | 3/1998 | Taylor |
| 5,743,905 A | 4/1998 | Eder et al. |
| 5,746,692 A | 5/1998 | Bacich et al. |
| 5,746,769 A | 5/1998 | Ton et al. |
| 5,749,891 A | 5/1998 | Ken et al. |
| 5,749,915 A | 5/1998 | Slepian |
| 5,755,773 A | 5/1998 | Evans et al. |
| 5,766,160 A | 6/1998 | Samson et al. |
| 5,766,203 A | 6/1998 | Imran et al. |
| 5,772,669 A | 6/1998 | Vrba |
| 5,795,288 A | 8/1998 | Cohen et al. |
| 5,807,236 A | 9/1998 | Bacich et al. |
| 5,843,158 A | 12/1998 | Lenker et al. |
| 5,876,398 A | 3/1999 | Mulier et al. |
| 5,885,601 A | 3/1999 | Sokal |
| 5,895,749 A | 4/1999 | Alvarez |
| 5,897,551 A | 4/1999 | Everett et al. |
| 5,925,059 A | 7/1999 | Palermo et al. |
| 5,935,137 A | 8/1999 | Saadat et al. |
| 5,935,145 A * | 8/1999 | Villar et al. .................... 606/191 |
| 5,954,715 A | 9/1999 | Harrington et al. |
| 5,968,052 A | 10/1999 | Sullivan, III et al. |
| 5,976,162 A | 11/1999 | Doan et al. |
| 5,979,446 A | 11/1999 | Loy |
| 6,019,757 A | 2/2000 | Scheldrup |
| 6,033,423 A | 3/2000 | Ken et al. |
| 6,042,590 A | 3/2000 | Sporri et al. |
| 6,066,139 A | 5/2000 | Ryan et al. |
| 6,068,626 A | 5/2000 | Harrington et al. |
| 6,080,152 A | 6/2000 | Nardella et al. |
| 6,096,052 A | 8/2000 | Callister et al. |
| 6,143,007 A * | 11/2000 | Mariant et al. ................. 606/151 |
| 6,145,505 A | 11/2000 | Nikolchev et al. |
| 6,156,742 A | 12/2000 | Mackenzie |
| 6,164,280 A | 12/2000 | Everett et al. |
| 6,176,240 B1 | 1/2001 | Nikolchev et al. |
| 6,178,354 B1 | 1/2001 | Gibson |
| 6,187,027 B1 | 2/2001 | Mariant et al. |
| 6,270,495 B1 | 8/2001 | Palermo |
| 6,286,510 B1 | 9/2001 | Ray et al. |
| 6,309,384 B1 | 10/2001 | Harrington et al. |
| 6,346,102 B1 | 2/2002 | Harrington et al. |
| 6,357,443 B1 | 3/2002 | Loy |
| 6,371,118 B1 | 4/2002 | Ray et al. |
| 6,401,719 B1 | 6/2002 | Farley et al. |
| 6,432,116 B1 | 8/2002 | Callister et al. |
| 6,513,528 B2 | 2/2003 | Burton et al. |
| 6,526,979 B1 | 3/2003 | Nikolchev et al. |
| 6,550,480 B2 | 4/2003 | Feldman et al. |
| 6,585,663 B1 | 7/2003 | Coley et al. |
| 6,589,230 B2 | 7/2003 | Gia et al. |
| 6,599,299 B2 | 7/2003 | Schultz |
| 6,634,361 B1 | 10/2003 | Nikolchev et al. |
| 6,679,266 B2 | 1/2004 | Nikolchev et al. |
| 6,684,884 B2 | 2/2004 | Nikolchev et al. |
| 6,705,323 B1 | 3/2004 | Nikolchev et al. |
| 6,712,810 B2 | 3/2004 | Harrington et al. |
| 6,726,682 B2 | 4/2004 | Harrington et al. |
| 6,758,831 B2 | 7/2004 | Ryan |
| 6,780,182 B2 | 8/2004 | Bowman et al. |
| 6,802,825 B2 | 10/2004 | Ackerman et al. |
| 6,871,650 B1 | 3/2005 | Nikolchev et al. |
| 7,014,645 B2 | 3/2006 | Greene, Jr. et al. |
| 7,073,504 B2 | 7/2006 | Callister et al. |
| 7,428,904 B2 | 9/2008 | Nikolchev et al. |
| 7,686,020 B2 | 3/2010 | Nikolchev et al. |
| 7,921,848 B2 | 4/2011 | Nikolchev et al. |
| 8,066,007 B2 | 11/2011 | Nikolchev et al. |
| 8,171,936 B2 | 5/2012 | Nikolchev et al. |
| 2001/0016738 A1 | 8/2001 | Harrington et al. |
| 2001/0041900 A1 | 11/2001 | Callister et al. |
| 2002/0013589 A1 | 1/2002 | Callister et al. |
| 2002/0072744 A1 | 6/2002 | Harrington et al. |
| 2003/0015203 A1 | 1/2003 | Makower et al. |
| 2003/0029457 A1 | 2/2003 | Callister et al. |
| 2003/0051735 A1 | 3/2003 | Pavcnik et al. |
| 2003/0199913 A1 | 10/2003 | Dubrul et al. |
| 2003/0220636 A1 | 11/2003 | Bowman et al. |
| 2004/0172051 A1 | 9/2004 | Ravikumar |
| 2004/0202694 A1 | 10/2004 | Burbank et al. |
| 2004/0204720 A1 | 10/2004 | Harrington et al. |
| 2004/0220585 A1 | 11/2004 | Nikolchev |
| 2004/0255958 A1 | 12/2004 | Harrington et al. |
| 2005/0033281 A1 | 2/2005 | Bowman et al. |
| 2005/0045183 A1 | 3/2005 | Callister et al. |
| 2005/0090855 A1 | 4/2005 | Ferrera et al. |
| 2005/0192616 A1 | 9/2005 | Callister et al. |
| 2005/0217680 A1 | 10/2005 | Callister et al. |

FOREIGN PATENT DOCUMENTS

| | | |
|---|---|---|
| CN | 1073088 A | 6/1993 |
| DE | 2404605 A1 | 8/1975 |
| DE | 2525650 A1 | 12/1976 |
| DE | 2537620 A1 | 2/1977 |
| DE | 2635863 A1 | 2/1977 |
| DE | 28 03 685 A1 | 8/1979 |
| DE | 2913036 A1 | 10/1980 |
| EP | 0 010 812 | 5/1980 |
| EP | 0105669 B1 | 9/1983 |
| EP | 0183372 A1 | 10/1985 |
| EP | 0241971 B1 | 3/1987 |
| EP | 0421966 A1 | 9/1990 |
| EP | 0541258 A1 | 5/1993 |
| EP | 0686382 A1 | 12/1995 |
| EP | 0739608 | 10/1996 |
| EP | 0 891 757 A2 | 1/1999 |
| GB | 1460077 | 12/1976 |
| GB | 1530565 | 11/1978 |
| GB | 2 010 728 | 7/1979 |
| GB | 2 038 186 | 7/1980 |
| GB | 2150439 A | 7/1985 |
| GB | 2 211 095 | 6/1989 |
| JP | 1-113045 | 5/1989 |
| JP | 5-269197 | 10/1993 |
| NL | 7810696 | 4/1980 |
| WO | WO 80/02369 | 11/1980 |
| WO | WO 83/00011 A1 | 1/1983 |
| WO | WO 88/09648 A1 | 12/1988 |
| WO | WO 94/07560 | 4/1994 |
| WO | WO 94/11051 | 5/1994 |
| WO | WO 9410936 | 5/1994 |
| WO | WO 94/24944 A1 | 11/1994 |
| WO | WO 94/26175 | 11/1994 |
| WO | WO 95/01123 | 1/1995 |
| WO | WO 95/25490 A1 | 9/1995 |
| WO | WO 96/22122 A1 | 7/1996 |
| WO | WO 96/40023 | 12/1996 |
| WO | WO 96/40024 | 12/1996 |
| WO | WO 97/08997 | 3/1997 |
| WO | WO 93/06884 | 4/1997 |
| WO | WO 97/12569 A1 | 4/1997 |
| WO | WO 97/13451 | 4/1997 |
| WO | WO 97/27893 | 8/1997 |
| WO | WO 97/46175 A1 | 12/1997 |

(56) References Cited

FOREIGN PATENT DOCUMENTS

| | | |
|---|---|---|
| WO | WO 97/49345 A1 | 12/1997 |
| WO | WO 98/26737 | 6/1998 |
| WO | WO 98/31308 A1 | 7/1998 |
| WO | WO 98/55046 | 12/1998 |
| WO | WO 94/06503 | 3/1999 |
| WO | WO 99/15116 | 4/1999 |
| WO | WO 00/13624 | 3/2000 |
| WO | WO 00/44323 A1 | 8/2000 |
| WO | WO 01/37760 A2 | 5/2001 |
| WO | WO 03/088879 | 10/2004 |
| WO | WO 2004/098469 | 11/2004 |

OTHER PUBLICATIONS

Brueschke, Erich E., "Reversible Occlusive Devices," J. Reproductive Medicine for the Obstetrician and Gynecologist, vol. 17, No. 2 (Aug. 1976).
Brandin J., "Ch. 31: Hydrogel Tubal Blocking Device: P-Block," Female Transcervical Sterilization (Gerald Zatuchni, M.D. et al., eds., Harper & Row 1983).
Brandin, J., "Hysteroscopy for Sterilization," Contraceptive Delivery Systems: An International Journal (1982).
Brandin, J., "Observations on the mode of action of an intratubal device, the P-block," Am. J. of Obst. & Gyn., (1987).
Cooper, "Hysteroscopic Sterilization", *Fertility Control*, 1985, Corson, et al., Eds., Little, Brown & Co. Boston, First Edition, pp. 119-131.
Corfman, "An Instrument for Transcervical Treatment of the Oviducts and Uterine Cornua", Obstetrics and Gynecology, 1996, 27(6):880-884.
Darabi, et al., "Collaborative Study on Hysteroscopic Sterilization Procedures: Final Report", *Risks, Benefits, and Controversies in Fertility Control*, 1978, Eds., Harper & Row, New York, pp. 81-101.
EPO Search Report for European Divisional Patent Application No. 07002727.1, mailed May 30, 2007, total 8 pages.
Fischer, Michael E. et al., "Silicone Devices for Tubal Occlusion: Radiographic Description and Evaluation," Radiology (Jun. 1984).
Free, Michael J. et al., "Technology for Mechanical Fallopian Tube-Blocking Device," Advances in Female Sterilization Techniques (Harper & Row 1976).
Hamou, J. et al., "Hysteroscopic Placement of Nylon Intratubal Devices for Potentially Reversible Sterilization," The Fallopian Tube: Basic Studies and Clinical Contributions (1986).
Hayashi, Motoyuki, "Ch. 28: Tubal Sterilization by Cornual Coagulation Under Hysteroscopy," Human Sterilization (Ralph Richart et al., eds. 1972).
Hosseinian, Abdol "31: Hysteroscopically Delivered Tubal Plugs," Reversal of Sterilization (John Sciarra et al., eds. Harper & Row 1978).
Hosseinian, et al., "Hysteroscopic Implantation of Uterotubal Junction Blocking Devices", Advances in Female Sterilization Techniques, 1976, Sciarra, et al., Eds., Harper & Row, New York, pp. 169-175.
J.F. Huka & K.F. Omran, "Ch. 27: Cauterization for Tubal Sterilization," Human Sterilization (Ralph Richart et al., eds. 1972).
Jay Cooper & Richard Houck, "Ch. 33: Study Protocol, Criteria, and Complications of the Silicone Plug Procedure," Female Transcervical Sterilization (Gerald Zatuchni, M.D. et al., eds., Harper & Row 1983).
Jay M. Cooper, "Hysteroscopic Sterilization," Clinical Obstetrics and Gynecology, vol. 35, No. 2 (Jun. 1992).
Kerin, J.F., "New Methods for Transcervical Cannulation of the Fallopian Tube," *International Journal of Gynecology and Obstetrics* 51 Suppl. 1 (1995) pp. S29-S39.
Leonard, Fred "Ch. 14: Polymer Implants," Female Sterilization (Ralph Richart et al., eds. 1972).
Luukkainen, Tapani et al., "15: Five Years' Experience with the Nova-T and T-Cu IUDs," Intrauterine Contraception (Gerald Zatuchni et al., 1984).
Malinak, Russell, M.D. et al., "Oviduct Occlusion Following Implantation of Proplast," Advances in Female Sterilization Techniques (John Sciarra et al., eds. Harper & Row 1976).
Manganiello, Paul D. et. al., "A Bipolar Radiofrequency Catheter Fails to Occlude a Feline Uterine Horn: A Model for Fallopian Tube Occlusion, " The Journal of the American Association of Gynecologic Laparoscopists, vol. 5, No. 3 (Aug. 1998).
Medical News, "Hysteroscope simplifies sterilization," J. of Am. Med. Assn., vol. 225, No. 6 (Aug. 6, 1973).
Neuwirth, Robert S. et al., "Hyesteroscopic Sterilization," Hysteroscopic Sterilization (John Sciarra et al. eds., 1974).
PCT Notification of Transmittal of International Preliminary Examination Report, PCT/US98/20031 dated Jun. 30, 2000, 5 pages.
PCT Notification of Transmittal of the International Preliminary Examination Report, PCT/US96/07486 dated Sep. 8, 1997.
PCT Notification of Transmittal of the International Search Report or the Declaration PCT/US96/07483 dated Sep. 5, 2006, 5 pages.
PCT Notification of Transmittal of the International Search Report or the Declaration PCT/US96/07486 dated Sep. 5, 1996, 5 pages.
PCT Notification of Transmittal of the International Search Report, PCT/US98/20031 dated Jan. 20, 1999, 5 pages.
PCT Written Opinion PCT/US96/07483 dated Jun. 20, 1997, 4 pages.
PCT Written Opinion PCT/US96/07486 dated May 19, 1997, 4 pages.
PCT Written Opinion PCT/US98/20031 dated Aug. 31, 1999, 4 pages.
Quinones et al., "Hysteroscopic Sterilization", Int. J. Gynaecol. Obstet., 1976, 14:28-34.
Richard Houck & Jay Cooper, "Hysteroscopic Tubal Occlusion With Formed-In-Place Silicone Plugs: A Clinical Review," Obst. & Gyn., vol. 62, No. 5 (Nov. 1983).
Richart et al., "Evaluation of Polymer Flock and Metal Alloy Intra-Tubal Device in Pigtail Monkeys", Contraception, 1978, 18(5):459-468.
Risquez, Francisco, et al., "Transcervical Tubal Cannulation, Past, Present, and Future," Fertility and Sterility, (1993) pp. 211-226.
Robert Neuwirth, Richard Levine, and Ralph Richart, "Hysteroscopic tubal sterilization," Am. J. of Obst. and Gyn., vol. 116, No. 1 (May 1, 1973).
Schmitz-Rode, Thomas et. al., "Experimental Nonsurgical Female Sterilization: Transcervical Implantation of Microspindles in Fallopian Tubes," Journal of Vascular and Interventional Radiology, vol. 5, No. 6 (Nov.-Dec. 1994).
Sciarra, "Heteroscopic Approaches for Tubal Closure", Research Frontiers in Fertility Regulation, 1980, Zatuchni, et al., Eds. Harper & Row, New York, pp. 270-286.
Sonmez et al., "Sterilization with fibrin sealant in a rabbit uterine horn model," Am J Obstet Gynecol., vol. 177, issue 3, 1997, pp. 573-578.
Sugimoto, Osamu, "Hysteroscopic Sterilization by Electrocoagulation," Hysteroscopic Sterilization (John Sciarra et al., eds., 1973.
Swope, C.H. "Ch. 23: Production of Clinically Useful Interactions of Laser Radiation With Tissue," Human Sterilization (Ralph Richart et al., eds. 1972).
Theodore Reed & Robert Erb, "Hysteroscopic Tubal Occlusion With Silicone Rubber," Obst. & Gyn., vol. 61, No. 3 (1983).
Thompson, Horace et al., "Evaluation of Experimental Methods of Occluding the Uterotubal Junction," Female Sterilization: Prognosis for Simplified Outpatient Procedures (Gordon Duncan et al, eds. 1972).
V. Rimkus & K. Semm, "Hysteroscopic Sterilization—a Routine Method?" Int'l. J. Fertility vol. 22 (1977).
Vancaillie, et al. "A New Method of Transcervical Female Sterilization: Preliminary Results in Rabbits," Fertility and Sterility vol. 51, No. 2, Feb. 1989, pp. 335-338.
Wilson, E.W., "Sterilization" *Baillière's Clinical Obstetrics and Gynecology*, vol. 10, No. 1, Apr. 1996, pp. 103-119.
Wilson, E.W., "The Evolution of Methods for Female Sterilization," *International Journal of Gynecology and Obstetrics* 51 Suppl. 1 (1995) pp. S3-S13.
Zipper, J. et al., "Suppression of fertility by intrauterine copper and zine in rabbits," Am. J. of Obstetrics and Gynecology (Oct. 15, 1969).

(56) References Cited

OTHER PUBLICATIONS

Sciarra, J.J., et al., eds., *Advances in Female Sterilization Techniques*, Harper & Row, Publishers, 1976, Title page and Table of Contents are enclosed herewith, pp. 169-181, 186-189.

Steptoe, P.C., "The Potential Use of Intratubal Stents for Reversible Sterilization," *Laparoscopy*, pp. 91-99, circa 1976.

Quinones, Rodolfo et al., "Tubal Electrocoagulation Under Hysteroscopic Control," Hysteroscopic Sterilization (John Sciarra et al., eds. 1973).

Brueschke, E.E., et al. "Transcervical tubal occlusion with a steerable hysteroscope: Implantation of devices into extirpated human uteri," *Am. J. Obstet. Gynecol.* vol. 127, No. 2, pp. 118-124, 1977.

Brundin, J., Transcervical sterilization in the human female by hysteroscopic application of hydrogelic occlusive devices into the intramural parts of the Fallopian tubes: 10 years experience of the P-block, *European Journal of Obstetrics & Gynecology and Reproductive Biology*, vol. 39, pp. 41-49, 1991.

Complete Chinese-to-English translation of Chinese Patent Publication No. CN 1047447A.

Conceptus Annual Report (1995) pp. 3, 5, 7, 9, 13-14 and 22.

Conceptus Annual Report (1996) pp. x, 3, 9 and 13-14.

Erb, R.A. et al. "Hysteroscopic Oviductal Blocking with Formed-in-Place Silicone Rubber Plugs," *The Journal of Reproductive Medicine*, pp. 65-68, Aug. 1979.

Gordon, A.G., et al., *Atlas of Gynecologic Endoscopy*, Mosby-Wolfe Press, 2nd Edition, 1995 (Title Page and Table of Contents are enclosed herewith).

Gupta, D.N. et al. "Antifertility Effect of an Intrafallopian Tubal Copper Device," *Indian J. Exp. Biol.*, vol. 14, pp. 316-319, May 1976.

Hamou, J. et al. "Hysteroscopic Reversible Tubal Sterilization," *ACTA Europaea Fertilitatis*, vol. 15, No. 2, 1984.

Reed, T.P., et al., "Tubal Occlusion with Silicone Rubber," *The Journal of Reproductive Medicine*, pp. 25-28, Jul. 1980.

Ross, P.L. et al., "Transcatheter Tubal Sterilization in Rabbits," *Investigative Radiology*, vol. 29, No. 5, pp. 570-573, 1994.

\* cited by examiner

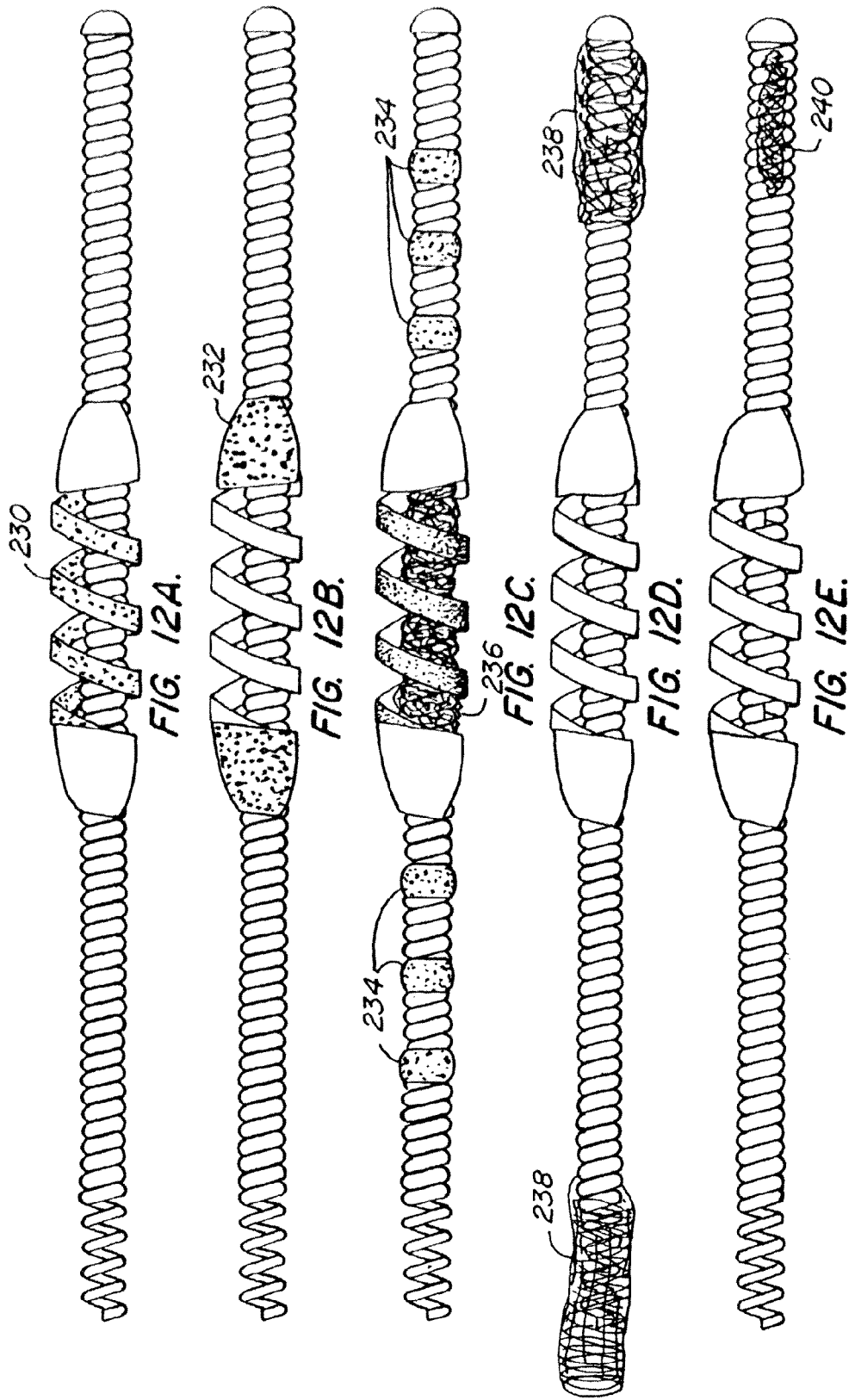

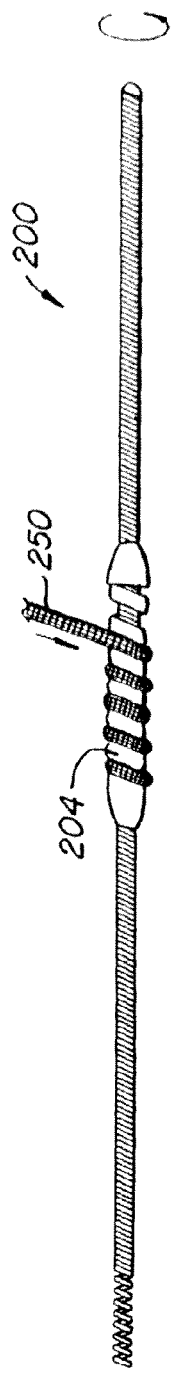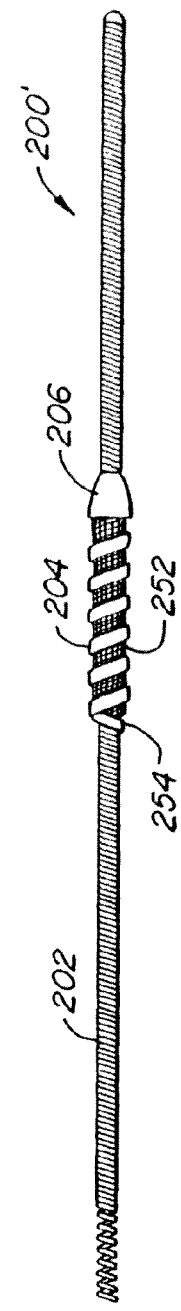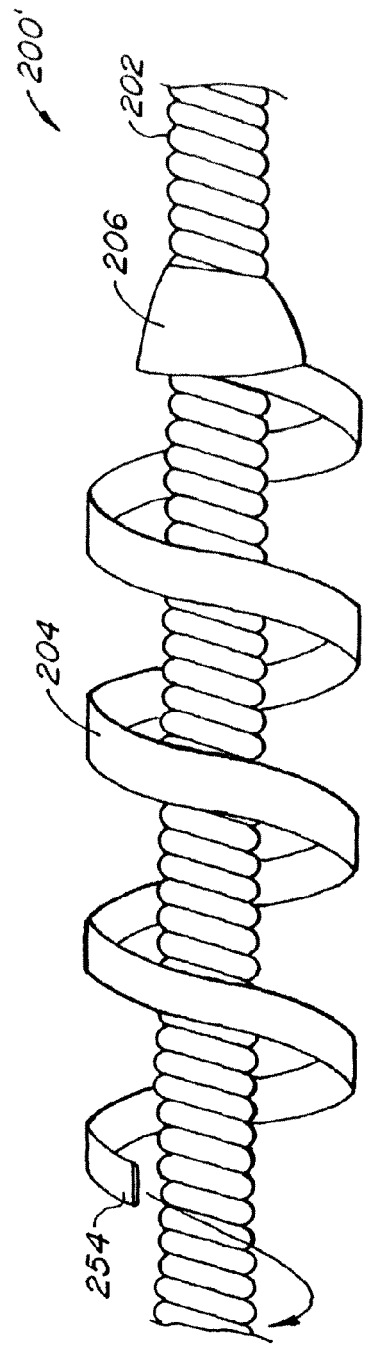

OCCLUSION DEVICES AND METHODS

CROSS-REFERENCES TO RELATED APPLICATIONS

This application is a continuation of pending U.S. patent application Ser. No. 13/294,758 filed on Nov. 11, 2011, which is a continuation of U.S. patent application Ser. No. 12/908,756 filed on Oct. 20, 2010, now U.S. Pat. No. 8,171,936, which is a continuation of U.S. patent application Ser. No. 10/600,298 filed on Jun. 20, 2003, now abandoned, which is a continuation-in-part of U.S. patent application Ser. No. 09/093,835, filed Jun. 8, 1998, now U.S. Pat. No. 6,705,323, which claims the benefit of priority from U.S. Provisional Application No. 60/059,861, filed Sep. 24, 1997, and is also a continuation-in-part of U.S. patent application Ser. No. 08/475,252 filed Jun. 7, 1995, now abandoned, and a continuation-in-part of U.S. patent application Ser. No. 08/474,779 filed Jun. 7, 1995, now U.S. Pat. No. 6,176,240. The full disclosures of U.S. patent application Ser. Nos. 09/093,835, 60/059,861 and 08/475,252 are incorporated herein by reference.

BACKGROUND OF THE INVENTION

1. Field of the Invention

The present invention relates generally to contraception, and more particularly to intrafallopian contraceptive devices and nonsurgical methods for their delivery.

Worldwide demand exists for safe, effective methods of both contraception and permanent sterilization. Although a variety of contraception and sterilization methods are available, all of the existing methods have limitations and disadvantages. Thus, the need for additional safe, low cost, reliable methods of contraception and permanent sterilization, both in developed and less developed countries, is widely recognized.

Many presently available contraception methods require significant user involvement, and user non-compliance results in quite high rates of failure. While the theoretical effectiveness of existing contraceptives, including barrier methods and hormonal therapies, is well established, overcoming user noncompliance to improve overall efficacy has proven difficult.

One form of contraception which is less susceptible to user noncompliance is the intrauterine device (IUD). IUDs have been found to have higher rates of reliability, and are effective for a longer period of time, than most other commercially available contraceptives. Unfortunately, IUDs are also associated with serious infectious complications. For this reason, the use of IUDs within the United States has decreased dramatically. Additionally, IUDs are subject to unplanned expulsion, and must be removed due to excessive pain or bleeding in a percentage of cases, further reducing the acceptance of the IUD as a contraceptive method. Interestingly, the efficacy of copper IUDs appears to be higher than that of non-metallic IUDs. The reason for this has not been fully explained.

Commercially available options for permanent sterilization include fallopian tube ligation and vasectomy. These methods are surgical, are difficult to reverse, and are not available to many people in the world. It is common knowledge that fertilization occurs in the fallopian tubes where the sperm and ovum meet. Tubal ligation avoids this by complete occlusion of the fallopian tubes.

It has previously been proposed to reversibly occlude the fallopian tubes, for example, by in vitro formation of an elastomeric plug, or otherwise anchoring a device on either side of the narrowest region of fallopian tube, called the "isthmus." Such fallopian tube occlusion methods appear promising; however, an unacceptably high percentage of the non-surgical devices proposed to date have become dislodged during previous studies. Even where non-surgical intrafallopian devices have remained in place, they have been found to be only moderately effective at preventing conception.

For these reasons, it would be desirable to provide effective, reliable intrafallopian devices for contraception and sterilization. It would be particularly desirable to provide highly effective intrafallopian devices which did not require surgery for placement. It would be especially desirable if such devices and methods allowed easy placement of the device, but were less susceptible to being dislodged than previously proposed non-surgical intrafallopian devices.

2. Description of the Related Art

The experimental use of a stainless steel intrafallopian device is described in Transcatheter Tubal Sterilization in Rabbits, Penny L. Ross, RT 29 "Investigative Radiology", pp. 570-573 (1994). The experimental use of an electrolytically pure copperwire as a surgical contraceptive intrafallopian device in rats was described in "Antifertility Effect of an Intrafallopian Tubal Copper Device", D. N. Gupta, 14 Indian Journal of Experimental Biology, pp. 316-319 (May 1976).

U.K. Patent Application Pub. No. 2,211,095 describes a uterine screw plug for blocking the fallopian tube. European Patent Application Pub. No. 0,010,812 describes a device for placement in the oviducts having enlargements at either end for anchoring the device. The same device appears to be described in Netherlands Patent No. 7,810,696.

The use of tubal occlusion devices is described in "Hysteroscopic Oviduct Blocking With Formed-in-Place Silicone Rubber Plugs", Robert A. Erb, Ph.D., et al., The Journal of Reproductive Medicine, pp. 65-68 (August 1979). A formed-in-place elastomeric tubal occlusion device is described in U.S. Pat. No. 3,805,767, issued to Erb. U.S. Pat. No. 5,065,751, issued to Wolf, describes a method and apparatus for reversibly occluding a biological tube. U.S. Pat. No. 4,612,924, issued to Cimber, describes an intrauterine contraceptive device which seals the mouths of the fallopian tubes.

German Patent No. 28 03 685, issued to Brundin, describes a device for plugging a body duct with a device which swells when in contact with a body fluid.

Alternative contraceptive devices are disclosed in co-pending U.S. patent application Ser. No. 08/474,779, the full disclosure of which is herein incorporated by reference.

SUMMARY OF THE INVENTION

The present invention provides intrafallopian devices and methods for their placement to prevent conception. The intrafallopian devices of the present invention are transcervically delivered and mechanically anchored within the fallopian tube to provide long term contraception, or alternatively permanent sterilization, without the need for surgical procedures or the risks of increased bleeding, pain, and infection associated with intrauterine devices (IUDs).

The intrafallopian devices of the present invention will often comprise a structure having a lumen-traversing region with a helical outer surface. The helical surface is mechanically anchored by a resilient portion of the structure which is biased to form an enlarged secondary shape, preferably forming distal and proximal anchoring loops. The anchoring loops help prevent the helical outer surface from rotating out of position, and also directly deter axial motion within the fallopian tube. In alternative embodiments, anchoring may be provided by a straight coil which is resiliently deflected by the axial curvature of the tortuous fallopian tube, and a radially expandable braid, malecott, or some other tubular structure may help affix the device within the fallopian tube.

The use of copper in the intrafallopian device of the present invention improves its efficacy as a contraceptive method. Devices formed from plastically deformable materials, however, are less readily restrained in the fallopian tube. Apparently, the large variation in the actual shape and dimensions of fallopian tubes does not provide reliable anchoring for a pre-formed deformable intrafallopian device. The intrafallopian device of the present invention therefore often comprises a resilient structure, usually a metallic coil, which includes a copper alloy or plating, ideally comprising an alloy including at least 75% copper. The coil material typically includes beryllium, zinc, stainless steel, platinum, a shape memory alloy, such as Nitinol®, or the like. Preferably, the coil is composed of an alloy of beryllium and copper.

Although the present device will generally result in occlusion, it need not completely occlude the fallopian tube to prevent the meeting of the sperm and ovum. Instead, in some embodiments, the presence of the copper on the resilient structure is sufficient to provide effective contraception. Hence, contraception can be provided by disrupting the normal architecture and/or function of the fallopian tube, despite the presence of an open lumen. This concept is referred to herein as "functional occlusion". As used herein, functional occlusion means that the device, when implanted in the fallopian tube, disrupts the normal architecture and/or functioning of the fallopian tube so as to inhibit fertilization and/or conception.

Conveniently, the present invention further comprises nonsurgical placement of such intrafallopian devices by transcervical introduction. The resilient structure is restrainable in a straight configuration, e.g., by use of a corewire, greatly facilitating and reducing the risks of introduction. Thus, the cost and dangers associated with existing surgical contraceptive and sterilization procedures are avoided. The resilient structure will often comprise a coil. In some embodiments, an element is disposed along the coil, and is adapted to incite a tissue reaction in the tubal tissues which inhibits conception. A distal anchor of the coil may be inserted into the ampulla, distal of the isthmus, while a proximal anchor is located in the ostium. These anchors prevent rotation of the device, and also help avoid axial movement. Alternatively, at least one of the anchors may be positioned anywhere past the ostium and within the fallopian tube, while the other extends into the uterus, depending on their length and configuration. Preferably, at least some anchoring is provided along the intramural to isthmic region of the fallopian tube. In some embodiments, electrosurgical attachment of an intraluminal device to a surrounding lumenal wall may provide effective anchoring even without loops and other anchoring structures. Electrical current may also be used to decouple the intrafallopian device from the delivery system, typically by electrolytically dissolving a solder bond. Current may also actuate an anchor, such as by releasing a resilient radially expandable tubular structure within the fallopian tube.

The present invention also provides improved contraceptive devices which incite a tissue reaction within the fallopian tube to prevent conception. This group of intrafallopian devices will often make use of a highly flexible coil structure to avoid damaging or penetrating through the delicate tubal tissues. The desired tissue reaction may be the result of the material of intrafallopian device, or may be incited by a coating, a surface treatment, a mechanical interaction between the device and the surrounding tubal wall, or the like. The tissue will often help impede conception by occluding the fallopian tube, by interrupting the transport mechanisms of the tubal tissues, and/or by restraining the intrafallopian tubal device within the tube. Specific tissue reactions which may provide these intended results include tissue ingrowth into the contraceptive device and/or the tubal lumen, scar tissue formation, sclerosing of the tubal tissues, and the like.

In one aspect, the invention provides a tissue reaction contraceptive device for use in a fallopian tube. The contraceptive device comprises a coil having a proximal end and a distal end and defining an axis therebetween. The coil is axially flexible and has a cross-section suitable for insertion into the fallopian tube. An element disposed along the coil is adapted to incite a tissue reaction in the tubal tissues adjacent the coil so as to inhibit conception.

In some embodiments, the element may promote ingrowth of the tubal tissues into the contraceptive device. For example, the element may include a braided or woven polyester, a micro-porous material or surface treatment, or the like. Alternatively, a sharp edged helical ribbon or other mechanical interaction element may incite the formation of scar tissue, or a surface coating of the coil may sclerose the tubal tissues, exciting formation of tough fibrous connective tissues which interfere with conceptive transport. In many embodiments, the presence of the contraceptive device in combination with the tissue reaction can provide effective contraception without having to rely on total occlusion of the fallopian tube.

In another aspect, the present invention provides a tissue ingrowth contraceptive device for use in a fallopian tube. The contraceptive device comprises a tubular retention structure having a proximal end, a distal end and an axis therebetween. The retention structure is axially flexible, and is insertable within the fallopian tube. A material which can incite ingrowth of the tubal tissue is attached to, and exposed radially from, the retention structure.

In the exemplary embodiment, the retention structure comprises a helical coil in which the ingrowth material is disposed. Such helical coils may optionally be radially expansible within the fallopian tube, thereby allowing the device to accommodate a wide variety of tubal physiologies. The ingrowth material may be in the form of braided or woven fibers of polyester, P.T.F.E., or the like.

In another aspect, the present invention provides a tissue ingrowth contraceptive device for use in a fallopian tube. The contraceptive device comprises a resilient elongate body having a proximal end and a distal end and defining an axis therebetween. A retention structure is disposed along the resilient body. The retention structure is adapted to restrain the resilient body within the fallopian tube. A bond affixes the retention structure to the resilient body. At least one of the resilient body, the retention structure, and the bond comprises a micro-porous material which promotes tissue ingrowth therein.

In another aspect, the present invention provides a contraceptive method comprising transcervically inserting a contraceptive device within a fallopian tube. The device is inserting by resiliently deflecting a distal body of the contraceptive device against a tubal wall, so that the distal body guides the contraceptive device axially along the fallopian tube. A tissue reaction is incited with an element of the contraceptive device in the tubal tissues. This tissue reaction affixes the contraceptive device within the fallopian tube.

The present invention also provides improved contraceptive devices, systems, and methods adapted for use in the widely varying geometry of the fallopian tube. In recognition of the wide variations in tubal physiology, the contraceptive structures of the present invention are radially expandable within the fallopian tube to engage the tubal wall. Surprisingly, the contraceptive devices of the present invention will often make use of tubular structures such as resilient helical coils. Such tubular devices will often effect contraception by disrupting the architecture and/or transport mechanisms of the tubal tissues, rather than relying entirely on total blockage of the tube. The passages through the tubular contraceptive devices of the present invention may optionally be occluded by promoting tissue ingrowth within the device, for example, by including woven or braided polyester fibers within a helical coil. Regardless, such tubular retention structures are capable of radially expanding against tubal walls throughout a wide range of tubal sizes to safely anchor the contraceptive device, without having to resort to protruding barbs or the like.

In one aspect, the present invention provides a contraceptive device for use in fallopian tube having a tubal wall. The contraceptive device comprises a tubular retention structure having a proximal end, a distal end, and an axis therebetween. The retention structure is radially expandable in situ from a narrow configuration (in which the retention structure has a first diameter which is suitable for axial insertion into the fallopian tube) so as to define a second, enlarged diameter. The expanded retention structure is adapted to engage the surrounding tubal wall and retain the contraceptive device within the fallopian tube.

In another aspect, the present invention provides a contraceptive device for use in a fallopian tube having a tubal wall. The contraceptive device comprises a conception inhibiting body which defines an axis. A helical coil is disposed about the body. A portion of the helical coil is movable relative to the body so that the helical coil can expand resiliently throughout a range of tubal cross-sectional sizes. Hence, the coil can radially engage the surrounding tubal wall and safely affix the contraceptive device within the fallopian tube.

The present invention also provides intrafallopian contraceptive devices having elongate coils which are substantially straight. Surprisingly, when such straight coils are positioned axially within the tortuous fallopian tubes, the bends imposed on the coil by the fallopian tube can result in resilient anchoring of the coil. Such straight coils are also highly advantageous when advancing the contraceptive device into (and within) the fallopian tube. Straight resilient coils can act as an integral guidewire during transcervical deployment of the device within the fallopian tube, thereby avoiding the delay associated with the sequential use of guidewires, tubal axis catheters, and the like.

The present invention provides an intrafallopian contraceptive device for use in a fallopian tube. The contraceptive device comprises an elongate coil having a proximal end, a distal end, and an axis therebetween. The axis is substantially straight when the coil is at rest, and the coil is axially resilient to facilitate insertion of the body axially into the tube. The device is adapted to be retained within the fallopian tube so as to inhibit conception.

In another aspect, the present invention provides an intrafallopian contraceptive device for use in a fallopian tube. The tube has a tubal wall with a tubal cross-section and an axial curvature. The contraceptive device comprises an elongate body having a proximal end and a distal end and defining an axis therebetween. The body has a cross-section suitable for axial insertion within the tubal cross-section. At least a portion of the body is straighter than the axial curvature of the fallopian tube. The body is sufficiently flexible to deflect against the tubal wall without injuring the tubal wall. The body is also sufficiently resilient to impose an anchoring force against the tubal wall when the straight portion flexes along the axial curvature of the fallopian tube.

In another aspect, the present invention provides a contraceptive device for use in a fallopian tube having an axis. The contraceptive device comprises a structure having a proximal end, a distal end, and an axis therebetween. The structure is adapted to provide effective tubal occlusion when disposed substantially coaxially within the fallopian tube. An elongate member is affixed to the occlusion structure. The member extends distally of the occlusion structure and is sufficiently flexible and axially resilient to help guide distal advancement of the occlusion structure within the fallopian tube.

In a contraceptive method provided by the present invention, an elongate resilient body is transcervically inserted into an axially curving fallopian tube so that the fallopian tube imposes an axial bend on the body. The bent body imposes an anchoring force which helps anchor the bent body within the fallopian tube. The body is anchored within the fallopian tube so that the affixed resilient body inhibits conception.

In another aspect, the present invention provides a contraceptive method comprising transcervically inserting an intrafallopian contraceptive device along the fallopian tube by guiding the contraceptive device with a distal guidewire-like structure of the contraceptive device. The device, including at least a portion of the guidewire-like structure, is retained within the fallopian tube so that the device inhibits conception.

In another aspect, the present invention provides a contraceptive kit. The kit comprises an intrafallopian contraceptive device and instructions for its use. The instructions describe and/or set forth the method steps of transcervically introducing the contraceptive device into a fallopian tube and affixing the contraceptive device within the tube. Optionally, a variety of delivery structures may also be provided in the kit, including guidewires, corewires, delivery catheters, and the like.

In yet another aspect, the invention provides an intrafallopian contraceptive system comprising an elongate delivery body having a proximal end and a distal end. A first energy conduit extends therebetween, and an intrafallopian structure near the distal end has a first cross-section. An energy source is coupled to the structure by the first conduit. Energy from the energy source reconfigures the structure to a second cross-section to restrain the structure within a fallopian tube and inhibit conception.

In a final aspect, the invention provides an elongate delivery body having proximal and distal ends with first and second conductors extending therebetween. An intrafallopian contraceptive structure is near the distal end of the delivery body. An electrical power supply can be coupled to the structure by the first and second conductors. This advantageous bipolar arrangement can, for example, allow actuation of a shape-memory alloy structure by transmitting current through at least a portion of the structure from a hand-held battery.

BRIEF DESCRIPTION OF THE DRAWINGS

FIGS. 12A-E illustrate a variety of intrafallopian contraceptive devices which are adapted to promote a tissue reaction that enhances the contraceptive efficacy of the device.

FIG. 13 illustrates a method for introducing a dense braid of fiber material into a helical coil of a contraceptive device.

DESCRIPTION OF THE SPECIFIC EMBODIMENTS

Figure 1:
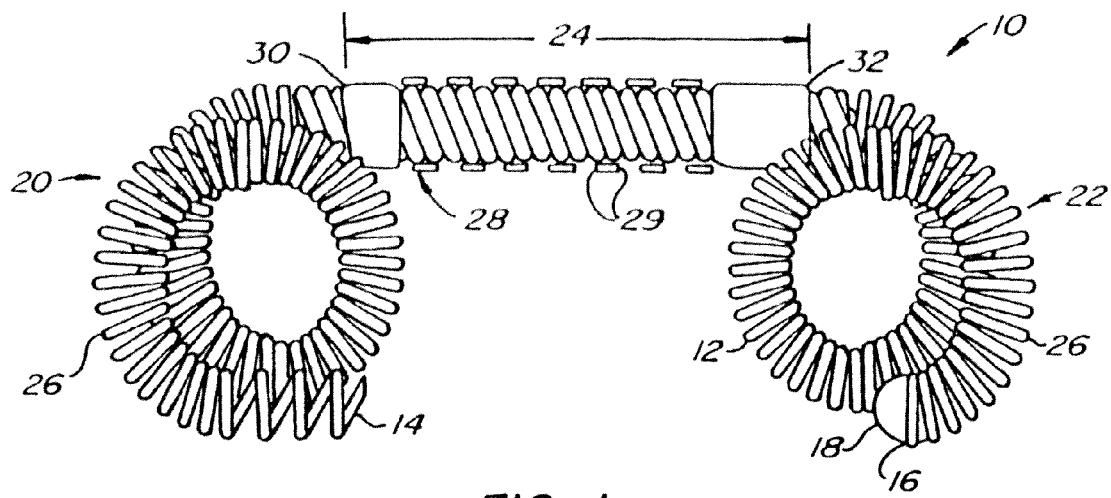
FIG. 1 illustrates a first embodiment of a contraceptive intrafallopian device according to the present invention.

The present invention encompasses a contraceptive intrafallopian device which can alternatively be used as both a permanent and a reversible means of contraception. The present contraceptive methods and devices minimize the danger of non-use which has limited the efficacy of prior art contraceptive techniques. Moreover, the location of the present devices within the fallopian tubes provides a reduced risk of the infectious complications, increased bleeding, and pelvic pain associated with intrauterine devices (IUDs). The location and the novel shape of the present intrafallopian device provides significant advantages over IUDs, which have been found to be susceptible to unplanned expulsion and removal due to excessive pain and bleeding. The present invention takes advantage of the increase in effectiveness associated with copper IUDs, providing a resilient structure including copper which may be transcervically positioned without the need for surgery.

Although the present contraceptive method is included within a group of contraceptive techniques generally referred to as fallopian tube occlusion methods, the present invention does not necessarily rely solely on blocking the fallopian tube to prevent fertilization. Instead, contraception is apparently provided by disrupting of ovum transport, the process of fertilization, and/or cleavage of the ovum. While the effect that copper has on these processes is not fully understood, it does appear that copper intrafallopian devices offer potentially significant increases in effectiveness over intrafallopian devices formed of other materials. Contraception may alternatively be provided or enhanced by a spermicidal agent attached to the device. Optionally, the present invention further encompasses devices which promote the growth of tissue within the tube to induce tubal occlusion, further inhibiting conception. In some embodiments, polyester fibers such as Dacron®, Rayon®, or the like, are bonded to the surface of the coil using a polymeric adhesive. The polyester fibers promote increased tissue growth around the coil, thus further reducing the possibility of expulsion of the device from the fallopian tube.

Conveniently, the present resilient structures are adapted to be releasably affixed over a corewire, the corewire restraining the resilient structure in a straight configuration. As the resilient structure has an outer diameter when in the straight configuration which is less than the inner diameter of the fallopian tube, the catheter containing the present intrafallopian device is easily transcervically introduced.

The present invention may be anchored within the isthmus of the fallopian tube, overcoming the unintended expulsion of the device and the resulting failure of the contraceptive method. Such intrafallopian device expulsion has been the single greatest factor limiting the efficacy of easily positioned intrafallopian contraceptive techniques. The present intrafallopian devices are generally elongate resilient structures preformed into secondary shapes. These secondary shapes will preferably form anchors proximally and distally of the narrowest portion of the fallopian tube, called the isthmus. The secondary shape preferably has a larger outer diameter than the inner diameter of the isthmus. Anchoring may also be possible with a structure spanning other portions of the tubal lumen, often between the ostial opening and the isthmus.

The present device is generally readily removed by snaring the resilient structure near the proximal end and pulling proximally on the resilient structure, thereby straightening the resilient structure and allowing it to be withdrawn without injuring the fallopian tube. Alternatively, an electrical current is applied to the device after it is positioned within the fallopian tube, providing permanent sterilization. Electrical current might also effect detachment of the device from the delivery system using a system similar to that described in U.S. Pat. No. 5,624,449, the full disclosure of which is incorporated herein by reference. In situ actuation of an anchor might be effected by releasing a resilient structure to expand in situ with a similar mechanism, or by a current induced phase change of a shape memory alloy (for example, causing a straight Nitinol® ribbon to curl within the fallopian tube with a current).

Referring now to FIG. 1, a first embodiment of the present contraceptive intrafallopian device 10 is formed from a resilient primary coil 12. Primary coil 12 has a proximal end 14 and a distal end 16, the latter having an atraumatic endcap 18.

Primary coil 12 further includes three portions: a proximal anchor portion 20, a distal anchor portion 22, and a lumen-traversing region 24. Proximal and distal anchors 20, 22 are biased to form anchoring loops 26, as described hereinbelow.

Lumen-traversing region 24 comprises a substantially straight portion of primary coil 12. A ribbon 28 is wound over the outer surface of primary coil 12 to provide a helical shape. Ribbon 28 includes sharp outer edges 29, which firmly anchor lumen-traversing region 24 in the fallopian tube wall when torque is applied to intrafallopian device 10. The ribbon is preferably formed of a high strength biocompatible metal, ideally being stainless steel. The ribbon is attached to primary coil 12 at a proximal joint 30 and a distal joint 32, which may be formed of solder, heat-shrink tubing, or the like.

Figure 2:
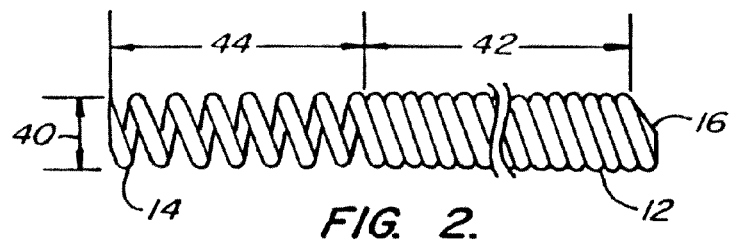
FIG. 2 illustrates a primary coil used in the contraceptive intrafallopian device of FIG. 1.

Referring now to FIG. 2, primary coil 12 is most easily formed in a straight configuration as a cylindrical coil or spring, preferably having an outer diameter in the range from 0.005 inch to 0.05 inch, and having a length in the range from 20 mm to 150 mm. Ideally, primary coil 12 has an outer diameter in the range from 0.01 inch to 0.05 inch and a length in the range from 30 mm to 125 mm.

Preferably, primary coil 12 is formed from a beryllium copper alloy wire. Beryllium copper provides the resilience necessary to avoid expulsion of the device, and also provides the increased effectiveness of a copper contraceptive intrafallopian device. Such a beryllium copper wire will typically have a diameter from 0.002 inch to 0.01 inch. To provide the increased efficacy of a copper intrafallopian device, primary coil 12 preferably comprises an alloy including 75% copper. Alternatively, primary coil 12 is formed from a resilient metal, such as stainless steel, platinum, a shape memory alloy, or the like. If such materials are used, primary coil 12 is preferably plated with copper or a copper alloy or otherwise has copper attached.

Primary coil 12 includes a body winding 42 and a thread winding 44. Body winding 42 is formed with the minimum possible pitch to increase the stiffness of primary coil 12. Thread winding 44 will typically comprise from 0.1 cm to 2.0 cm adjacent to proximal end 14, and will have a pitch roughly twice that of body winding 42.

Figure 3:
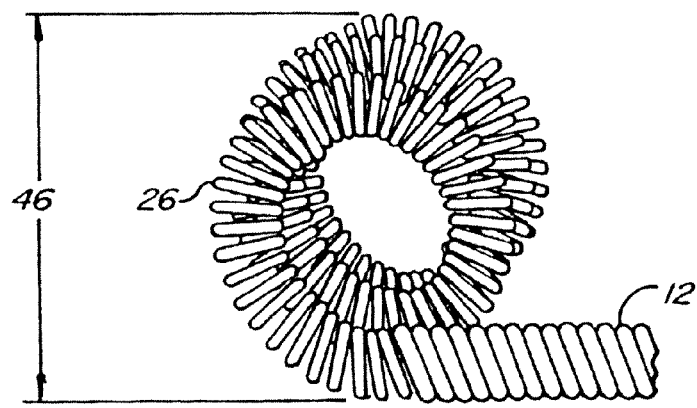
FIG. 3 illustrates a secondary coil which has been imposed on a primary coil as used in the contraceptive intrafallopian device of FIG. 1.

Referring now to FIG. 3, the proximal and distal anchors are formed by imposing a bent secondary shape on selected portions of primary coil 12. The secondary shape preferably comprises loops 26 formed by bending primary coil 12, and heat treating the primary coil while it is bent. A wide variety of secondary shapes may be used, including sinusoidal curves, alternating loops, or loops separated by straight sections so as to form a "flower coil," as more fully described in co-pending U.S. patent application Ser. No. 08/474,779, the full disclosure of which is herein incorporated by reference. In most cases, the bent secondary shape will have an outer cross-section 46 which is larger than the fallopian tube to provide effective anchoring.

Figure 4:
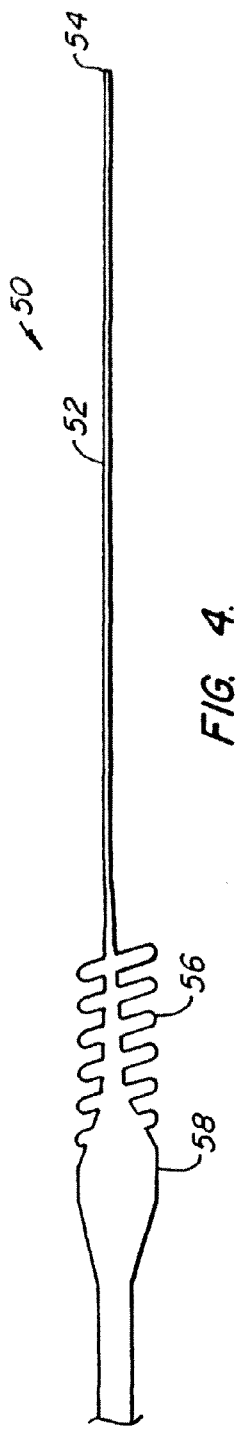
FIG. 4 illustrates a corewire for use with the contraceptive intrafallopian device of FIG. 1.

Referring now to FIG. 4, a corewire 50 for use with intrafallopian device 10 (FIG. 1) comprises a resilient wire 52 which tapers towards a distal end 54. Wire 52 is sufficiently stiff to restrain intrafallopian device 10 in a straight configuration, typically comprising stainless steel, platinum, or the like. A short section of coil forms corewire threads 56 attached at threadjoint 58. Threads 56 match the windings and pitch of threadwindings 44 of primary coil 12.

Figure 5:
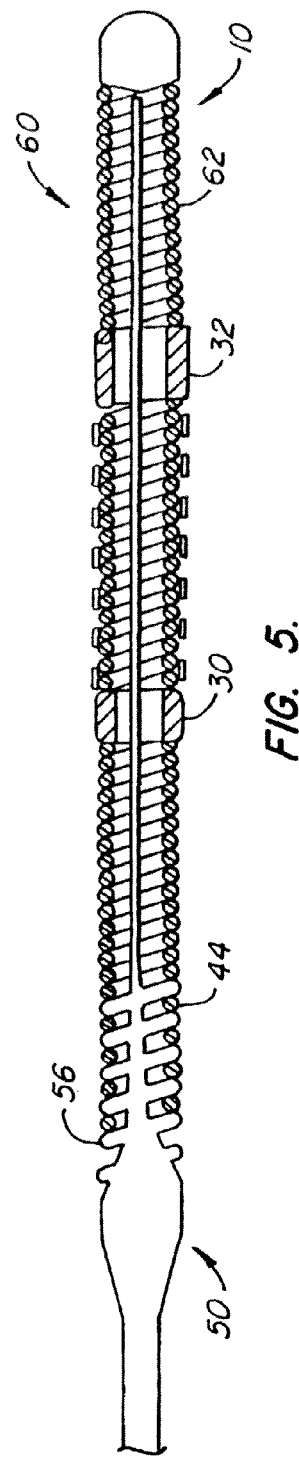
FIG. 5 is a cross-sectional view of a contraceptive delivery system having the contraceptive intrafallopian device of FIG. 1.

Referring now to FIG. 5, an intrafallopian contraceptive system 60 comprises corewire 50 inserted within a lumen 62 through intrafallopian device 10. Intrafallopian device 10 is releasably attached by engaging thread windings 44 with threads 56. Thus, intrafallopian device 10 is disengaged by torquing a proximal end of corewire 50 once intrafallopian device 10 is in position.

Figure 6:
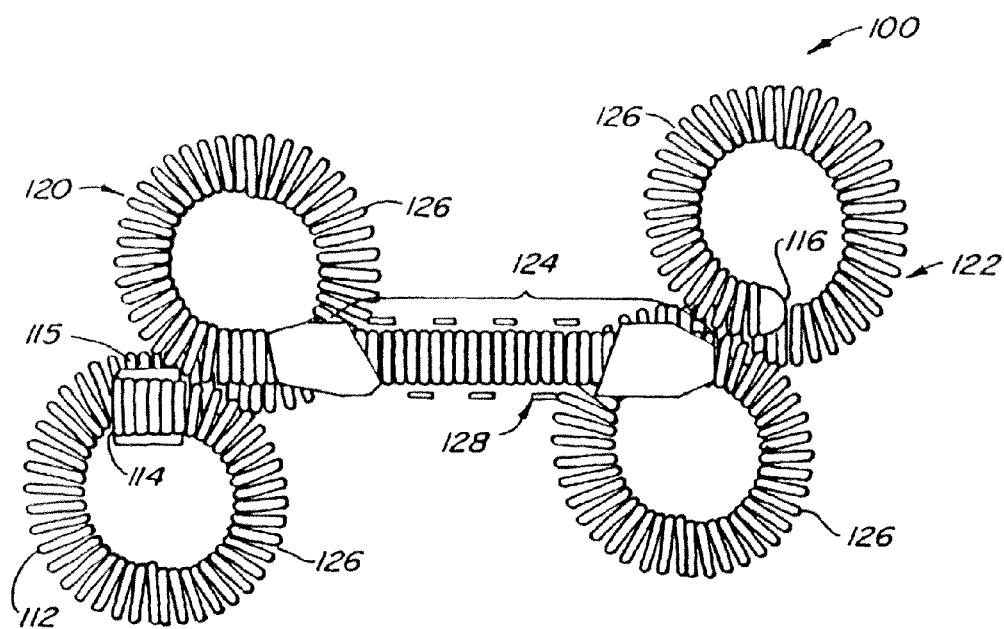
FIG. 6 illustrates an alternative embodiment of the present contraceptive intrafallopian device.

Referring now to FIG. 6, an alternative embodiment of the present intrafallopian device is again formed from a resilient primary coil 112 having a proximal end 114 and a distal end 116. The former includes a friction fitting 115. Primary coil 112 again includes three portions: a proximal anchor portion 120, a distal anchor portion 122, and a lumen-traversing region 124. Proximal and distal anchors 120, 122 are here biased to form opposed anchoring loops 26, thereby increasing the relaxed overall cross-section of the proximal and distal anchors. A ribbon 128 is wound over the outer surface of primary coil 112 to provide a helical shape, as described above.

Figure 7:
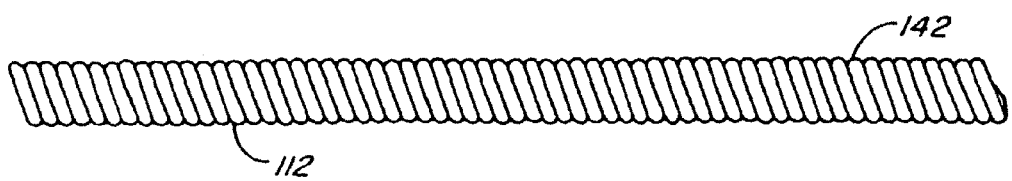
FIG. 7 illustrates a primary coil used in the contraceptive intrafallopian device of FIG. 6.

Referring now to FIG. 7, primary coil 112 comprises a uniform body winding 142. The secondary shape is imposed on the straight cylindrical coil as opposed loops 126, or alternatively as multiple loops of a flower coil.

Figure 8:
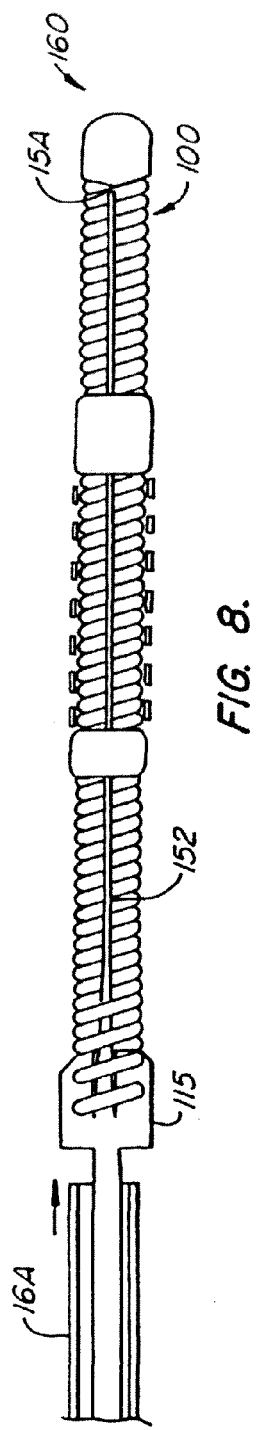
FIG. 8 schematically illustrates a contraceptive delivery system including the contraceptive intrafallopian device of FIG. 6.

Referring now to FIG. 8, an intrafallopian contraceptive system using alternative intrafallopian device 100 includes a corewire 152 which tapers towards a distal end 154. Friction fitting 115 fittingly engages corewire 152, which restrains primary coil 112 in a straight configuration. A release catheter 164 is slidably disposed over corewire 152 proximally of alternative intrafallopian device 100, allowing the device to be released by withdrawing corewire 152 relative to the release catheter.

Figure 9:
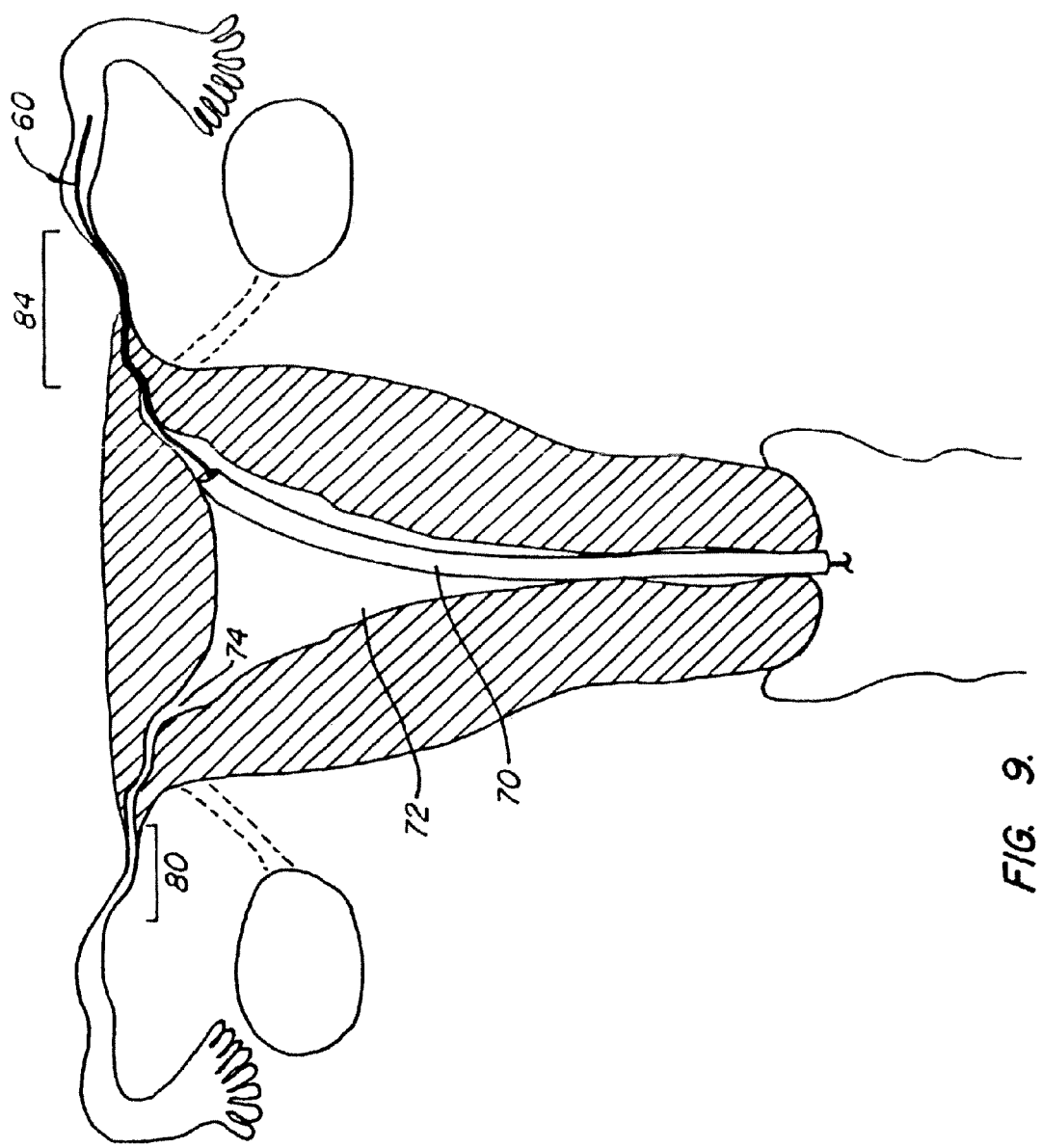
FIGS. 9 and 10 illustrate a method of delivery of a contraceptive intrafallopian device according to the present invention.
Figure 10:
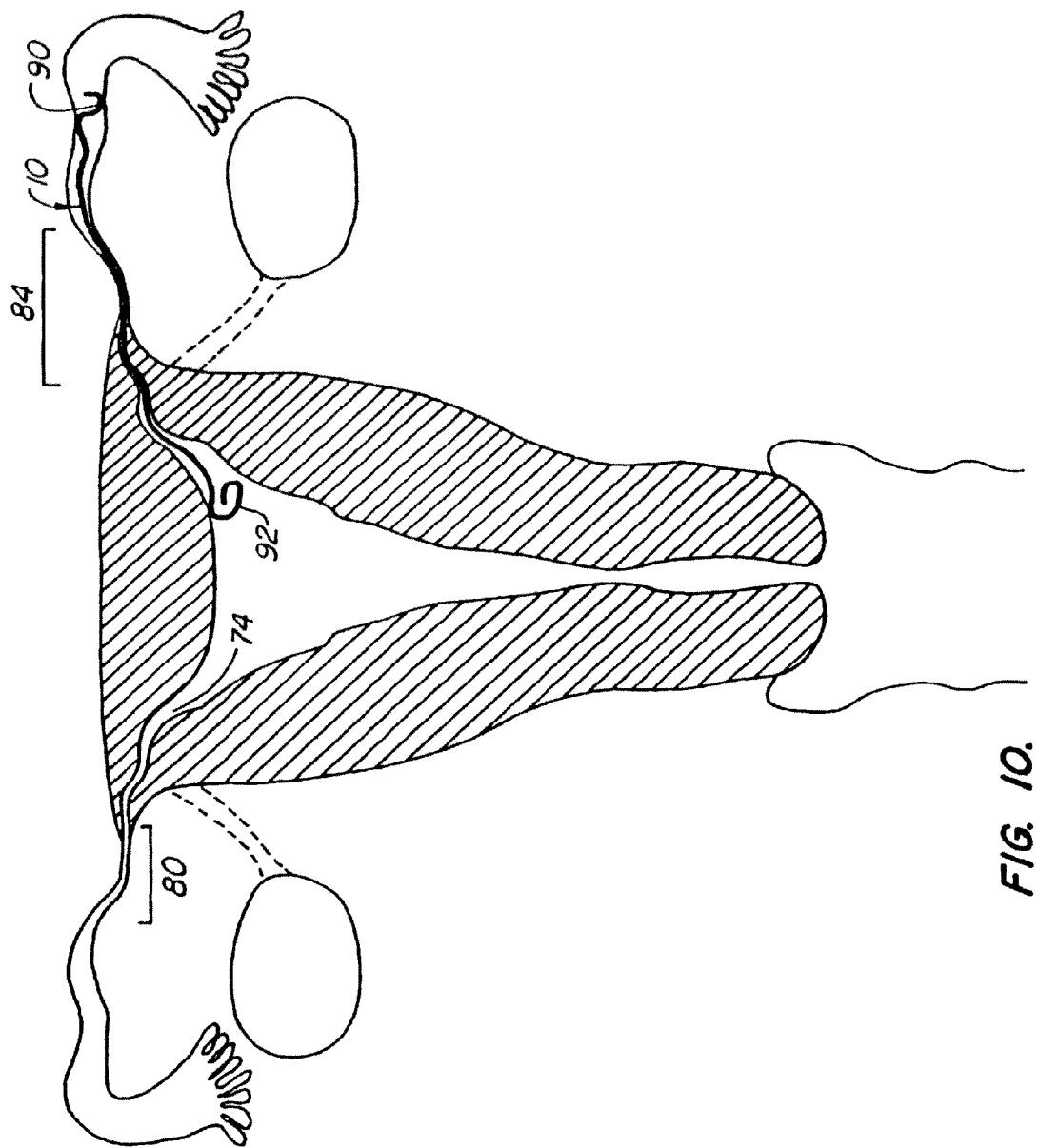

Use of the present contraceptive intrafallopian device will be described with reference to FIGS. 9 and 10. A uterine introducer canula 70 is inserted transcervically through a uterus 72 to the region of an ostium 74. Alternatively, a hysteroscope may be used in place of canula 70, or an echogenic and/or radiopaque device might be placed under sonographic or radiopaque guidance.

Intrafallopian contraceptive system 60 is advanced distally of introducer cannula 70 and maneuvered through the fallopian tube, preferably until intrafallopian device 10 extends distally of the isthmus. Optionally, intrafallopian contraceptive system 60 is self-guided, with corewire 52 bent near distal end 54 to assist intraluminal maneuvering. Alternatively, a guide wire and catheter are advanced into the fallopian tube first, and the guide wire is replaced with intrafallopian contraceptive system 60. In either case, the intrafallopian device will generally be axially positioned with lumen-traversing region 24 within a target region 84 adjacent to isthmus 80. Preferably, at least one loop of distal anchor 22 is distal of target region 84, and at least one loop of proximal anchor 20 is proximal of target region 84 to form the distal and proximal anchor bends.

Once intrafallopian device 10 is properly positioned, corewire 50 is torqued to set ribbon 28 in the tubal wall. The corewire may then be unthreaded from intrafallopian device 10 by rotating the corewire in the opposite direction, disengaging threads 56 from thread windings 44. The corewire is then free to slide proximally, releasing the primary coil. As the distal end of the primary coil is released, a distal anchor bend 90 is formed. Similarly, a proximal loop forms a proximal anchor bend 92. The anchor bends help to axially restrain the device within the fallopian tube, and also prevent rotation around the helical shape of lumen-traversing region 24. As seen in FIG. 10, the loops need not assume their relaxed form to provide effective distal or proximal anchors.

The present invention further encompasses permanent sterilization by passing a current through the corewire to the intrafallopian device prior to withdrawing the corewire. Fallopian tube tissue in contact with the intrafallopian device is desiccated, and thus attached to the present intrafallopian device. This action also causes permanent tubal damage, leading to the formation of scar tissue which encapsulates the intrafallopian device and causes permanent occlusion of the tubal lumen. Clearly, the corewire/primary coil interface must be conductive to allow the present non-surgical method of permanent sterilization.

The intrafallopian contraceptive methods and devices of the present invention can provide highly effective contraception even when the contraceptive device does not totally occlude the lumen of the fallopian tube. To minimize distention of the delicate tubal tissue, the present invention will often leave some open lumen within the fallopian tube, at least when initially deployed. In fact, these contraceptive devices will often comprise perforate tubular structures having lumens. Nonetheless, contraception can be provided by disrupting the normal architecture and/or function of the fallopian tube, despite the presence of an open lumen. This concept is referred to herein as "functional occlusion". As used herein, a device which provides functional occlusion means that the device, when implanted in the fallopian tube, disrupts the normal architecture and/or functioning of the fallopian tube so as to inhibit fertilization and/or conception.

The size of an occlusive device required to provide functional occlusion may depend on the material of the device, the position the device is to be deployed within the fallopian tube, the interaction between the device and the surrounding tubal wall, and the like. For example, intrafallopian contraceptive structures which include fibers of polyester may incite ingrowth of the tubal tissues into the device. As a result of this tissue/device interaction, a relatively small device which promotes ingrowth may be capable of providing effective occlusion. In fact, such a device may be capable of providing total occlusion by inciting sufficient ingrowth so that the hyperplastic tubal walls, in combination with the device, block all passage through the tubal lumen. Hence, relatively small, easily inserted structures may effectively inhibit conception without the danger of distending the tubal wall.

Figure 11A:
FIGS. 11A-D illustrate intrafallopian contraceptive devices having straight primary coils, together with associated delivery devices and systems.

One easily inserted intrafallopian contraceptive structure which may be capable of providing effective tubal occlusion is illustrated in FIG. 11A. A straight contraceptive device 200 includes a straight primary coil 202 around which is disposed a secondary helical coil 204 as described above. Secondary coil 204 is affixed to primary, coil 202 at a pair of bonds 206. As illustrated above in FIG. 6, the secondary helical coil may have an inner surface which is larger than the outer surface of primary coil 202, which may facilitate embedding the corners of the secondary coil in the surrounding tubular wall. However, unlike the intrafallopian devices described hereinabove, straight device 200 remains substantially straight between a proximal end 208 and a distal end 210 when the primary coil is at rest.

Primary coil 202 will typically be formed from wire having a diameter of between about 0.002 and 0.009 inches, by winding the wire to form a coil having a diameter between about 0.010 and 0.040 inches. Primary coil 202 will often have a length of between 2.9 and 3.5 cm. The ribbon used to form secondary helical coil 204 will generally have a width between about 0.005 and 0.020 inches, and a thickness of between about 0.0005 and 0.005 inches.

In the exemplary embodiment, straight device 200 includes a primary coil 202 having a total length of between about 3.0 and 3.35 cm. The exemplary primary coil 202 is wound from platinum wire, the platinum wire having a thickness of 0.005 inches, which is wound to provide a primary coil having an outer diameter of about 0.018 inches and a length of about 3.0 cm. Secondary coil 204 is formed from a platinum ribbon having a width of 0.012 inches and a thickness of 0.002 inches. Bonds 206 comprise gold solder and secondary coil 204 has a length of about 0.5 to 1.0 cm and an outer diameter of between about 0.035 to 0.040 inches when affixed to the primary coil 202. Solder is also used to form an atraumatic tip at distal end 210.

Figure 11B:
Figure 11C:
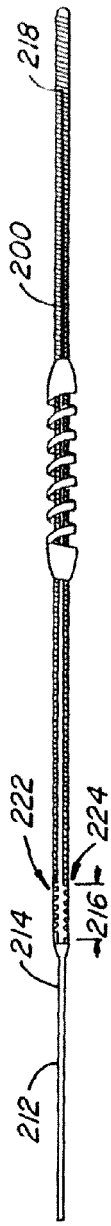

Referring now to FIGS. 11B and 11C, a self-guiding contraceptive delivery system 212 includes straight contraceptive device 200 and a flexible tip corewire 214. As described above, threads 216 on flexible tip corewire 214 mate with the proximal end 208 of straight contraceptive device 200, the threads ideally comprising a stainless steel coil having approximately the same dimensions as primary coil 202 and affixed to the corewire with yet another gold solder joint 206.

Advantageously, distal end 218 of corewire 214 need not have sufficient stiffness and strength to restrain a coil biased to form a bent secondary shape. As a result, the thickness of corewire 214 may be optimized to enhance the trackability and pushability of self-guided contraceptive system 212, thereby enhancing the ability of the contraceptive system to act as its own guidewire.

Delivery of the contraceptive device is facilitated by using a corewire having a relatively long, stiff proximal section and a relatively short, flexible section, the flexible section typically being tapered as illustrated. The thickness and material properties of these sections are selected to provide enough column strength to allow corewire 214 to advance straight device 200 within the fallopian tube, but enough flexibility at the distal end of the delivery system for distal end 210 to navigate the tortuous fallopian tube. A relatively thick proximal section also improves the torque transmission capabilities of the wire, particularly for torquing and embedding the outer coil against the tubal wall.

Proximal section 220 of corewire 214 will preferably be flexible enough for delivery through a flexible catheter and/or through the working channel of an endoscope. The corewire will generally comprise a material which resists kinking and resiliently returns to its original shape, ideally comprising a shape memory alloy such as Nitinol® or a treated stainless steel. Such resilience may be tailored to enhance the ability of the delivery system to access the tubal ostium and advance the contraceptive device into the fallopian tube. In some embodiments, corewire 214 will be capable of transmitting heat, electrical current, and/or some other energy which induces scarring, electrocautery, or the like, so as to attach the contraceptive device within the fallopian tube. Alternatively, the transmitted energy may decouple the device from the corewire, for example, by melting a coupler.

In a particularly advantageous aspect, threads 216 of delivery system 200 may be adapted to enhance visualization of the detachment process. For example, a first portion of the threads 222 may be a first color (such as green) while a second portion of the threads 224 may be a second color which contrasts sharply with the first color (such as red). As they are near the proximal end of the device, threads 216 will often be more visible than the remainder of the contraceptive device. The threads may even protrude through the tubal os into the uterus for viewing through the hysteroscope. By visually monitoring highly contrasting colors of the thread portions through the hysteroscope, the attending physician will be provided with direct feedback on the decoupling process. The thread portions may be colored by coating, anodizing, oxidation, polishing, the use of differing materials, or the like. A stripe or other mark may also be provided on the delivery wire to help monitor rotation. Alternative embodiments may use threads having high contrast under imaging.

Still further capabilities may be incorporated into the delivery system. For example, a "smart" delivery device may be able to sense its position within the fallopian tube magnetically, electrically, optically, ultrasonically, or the like. Similarly, the deployed device may incorporate structures which allow the physician to remotely verify the position and presence of the device without having to access the fallopian tube (e.g., using a magnetic sensor, impedance, and/or radio activity).

In the exemplary embodiment, corewire 214 comprises a shape memory alloy such as Nitinol®. Proximal portion 220 of corewire 214 has a thickness of between about 0.018 and 0.040 inches, ideally being about 0.035 cm, and the corewire tapers over a length of about 5.0 cm to a minimum thickness of between about 0.002 and 0.008 inches, typically about 0.003 inches at distal end 218.

Figure 11D:
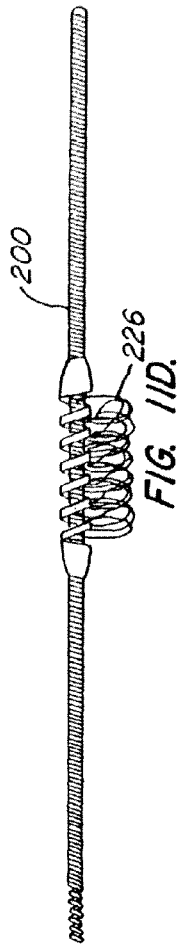

One method for attaching polyester fibers 226 to straight contraceptive device 200 is illustrated in FIG. 11D. As described above, such polyester fibers promote tissue ingrowth, which can help affix the device within the fallopian tube. Additionally, such tissue ingrowth may also help to further occlude the lumen of the fallopian tube. Fibers 226 are shown tied in loops around the secondary coil, ideally using between about 5 and 7 loops and fiber.

A wide variety of alternative mechanisms may be employed to incite a tissue reaction which enhances the functional occlusion of the intrafallopian contraceptive device. For example, materials such as collagen, hydroxyapatite, solid or fibrous PTFE, or the like may be used. Biodegradable coatings may cause tissue ingrowth or scarring, and then degrade to leave a fully or partially occluded lumen. In some embodiments, the engagement between outer coil 204 and the tubal wall injures the epithelial tissues, and the healing process results in the formation of scar tissues which interfere with the functioning of the fallopian tube.

A variety of alternative ingrowth promoting intrafallopian contraceptive devices are illustrated in FIGS. 12A-E. Generally, each of these devices includes some element which promotes ingrowth of tubal tissues therein. A porous secondary coil 230 may be formed of a porous metal, ideally comprising a micro-porous shape memory alloy such as Nitinol®. In some embodiments, ingrowth bonds 232 may be formed of, or coated with, a material such as bioglass, ceramics, or the like so as to promote tissue ingrowth, so that the entire device may promote ingrowth. Surface treatments may also encourage ingrowth. For example, blasting a surface with small particulates can create a somewhat devoted and porous texture. Such porous textures at the surface, with micron-sized pores, may produce the desired tissue reaction. Alternative embodiments may include an open cell ingrowth promoting structure, such as the open cell foams used to attach some breast implants.

In some embodiments, discrete bodies 234 may be formed as rings or annular beads using any of the above listed tissue ingrowth materials, coatings, or treatments. Wound, wrapped, or braided fiber material 236 may also be disposed between the primary and secondary coils, the fiber material typically comprising a polyester such as Dacron®, Vicril®, or the like. Dense fiber materials within the device may enhance the reaction and/or ingrowth of the surrounding tubal tissues, and also decreases the amount of open space within the device, thereby minimizing any prosthetic lumen. Fiber material 236 may also be in the form of a thick felt, or may simply be spun with several layers of windings.

Still further alternative ingrowth promoting elements are possible, such as tubular fabric 238 of felt, braided or woven material, or the like. Tubular fabric 238 provides an open conduit at the proximal end of the device to avoid impeding with the removal of the corewire, and the outer diameter of the tubular fabric will preferably be less than the outer diameter of the secondary coil. In some embodiments, simply providing an internal fabric 240 in the form of a textile mesh or felt inside the primary coil may be sufficient to incite ingrowth of the tubal tissues into the coil, affixing the coil in place and providing functional occlusion of the fallopian tube.

Referring now to FIG. 13, a particularly advantageous method for producing a contraceptive device having a dense fiber braid 250 is illustrated. Dense fiber braid 250 is initially formed by wrapping several layers of fiber around a mandrel. After about fifteen layers of fiber have been wrapped over the mandrel, the wound fiber is slid off the mandrel, and the windings are processed to form the braid. The braid is affixed to contraceptive device 200 adjacent one of the bonds, and the fiber braid is then wound between the windings of secondary coil 204. As a result, at least a portion of fiber tube 250 is disposed in the annular space between the primary coil and secondary coil 204. Often times, some portion of the fiber will also extend radially beyond secondary coil 204, as illustrated.

The use of dense fiber braid 250 provides a much greater amount of fiber and a more radially compact, easily deployable assembly than a structure which includes loops tied radially around the secondary coil. Such densely packed fiber thereby makes use of an otherwise open space, and the enhanced amount of fiber should provoke a more robust tissue reaction. Specifically, dense fiber braid 250 will have a smaller pore size, which is generally advantageous for tissue ingrowth. This combination of an enhanced tissue reaction, with a less axially open design, would appear to provide significant advantages for functional occlusion of the fallopian tube.

A still further alternative intrafallopian contraceptive device 200' is illustrated in FIG. 14. Alternative device 200' includes several of the same primary structures described hereinabove regarding straight contraceptive device 200, but makes use of a fiber tube 252 to provide the advantages of high fiber density and a small radial package. In this embodiment, the fiber is again wrapped around a mandrel several times (ideally about 15 times) and then removed as a fiber tube. Tube 252 is slid off the mandrel and onto the primary coil. The tube may be positioned before or after secondary coil 204 is attached at bond 206, and will generally occupy the annular space between the primary and secondary coils. The ends of tube 252 can be tied to keep the tube in position during delivery.

Alternative contraceptive device 200' also differs from the previous structures in that secondary coil 204 has a free end 254 which is not affixed to primary coil 202. As free end 254 can move relative to primary coil 200, secondary coil 204 can expand radially well beyond bond 206, and can also be radially compressed to provide a very small outer diameter during delivery of the device. Hence, the diameter of secondary coil 204 in alternative device 200' provides a highly radially variable tubular structure which can easily adapt to a wide variety of tubal lumen cross-sectional sizes to retain the contraceptive device within the fallopian tube.

A highly radially expandable tubular retention structure has several significant advantages. First, the structure can be inserted in a narrow profile configuration and radially expanded within the fallopian tube to provide a secure anchor with minimal danger of protruding through the delicate tubal wall. Additionally, the stiffness of the helical secondary coil can be tailored to provide the appropriate engagement force and/or damage to the wall tissue so as to provoke the desired tissue reaction, whether it be scar tissue formation, ingrowth, or the like. Torquing of a free ended helical coil may also be used to adjust the outer diameter during delivery.

Figure 14B:
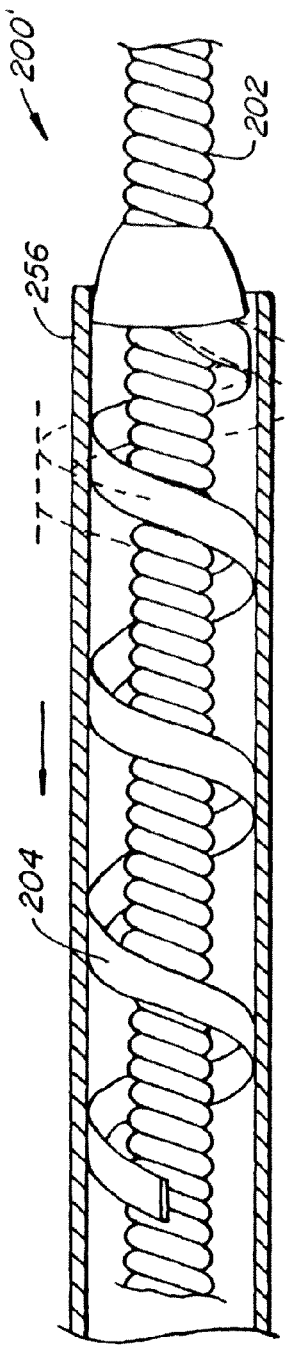
FIGS. 14-14E illustrate helical coils which adapt to varying tubal sizes to enhance retention of the contraceptive device within the fallopian tube.
FIGS. 14F, 14G, and 14H show structures for releasably restraining a coil.
Figure 14C:
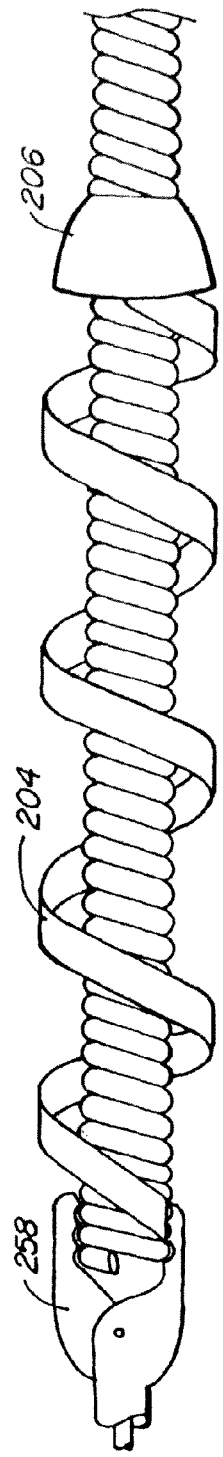

The enhanced variability in outer diameter provided by an outer coil 204 having a free end 254 can be understood with reference to FIGS. 14A-C. Generally, outer coil 204 will here have an outer diameter of over about 0.080 mm in its relaxed state, the outer diameter of the secondary coil preferably being biased to form a helix with an outer diameter of about 1.0 mm when at rest, and will ideally be compressible to an outer diameter of 0.1 mm for insertion. Outer coil 204 of alternative device 200' may be easily radially compressed by drawing free end 254 proximally away from bond 206, by wrapping the free end around primary coil 202, or by some combination of both.

As illustrated in FIGS. 14B and C, the device may be restrained in a small diameter configuration by a delivery catheter 256, by articulatable jaws 258, or the like. Regardless, secondary coil 204 will generally be restrained until the device is positioned within the fallopian tube, and will then be released in situ by axially withdrawing catheter 256, articulating jaws 258, or the like. Still further alternative in situ release mechanisms are possible, such as dissolving or dissipating a crystal or electrolytic coating which radially restrains the secondary coil, a phase change in a shape memory alloy, or the like, as described above. It should be noted that the free ended secondary coil is illustrated in FIGS. 14A-C without the optional dense fiber tube of FIG. 14A for clarity. Nonetheless, the enhanced radial variability provided by a free ended helical coil (or by other perforate tubular structures) may be either used alone or combined with other tissue reaction structures described hereinabove to provide functional occlusion and contraception.

Figure 14D:
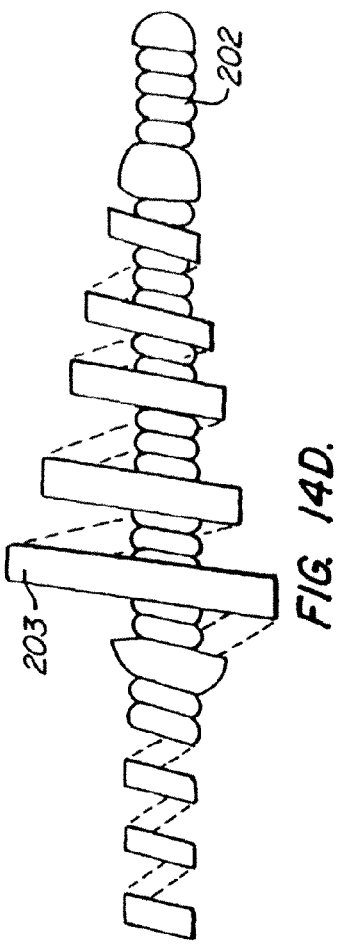
Figure 14E:
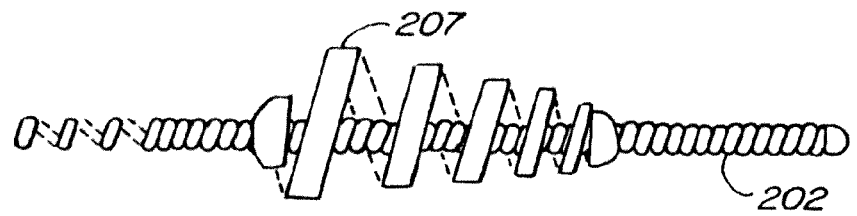

Alternative helical retention structures are illustrated in FIGS. 14D and 14E. A tapered coil 203 may be advanced distally, either axially or by rotationally threading the device, to embed the structure into a tapering portion of the tubal wall. The device can accommodate a variety of tubal sizes, as it need only be advanced until proper engagement has been achieved. Variable stiffness along the outer coil may be provided by a coil formed with a tapering ribbon 207, or the like.

Figure 14F:
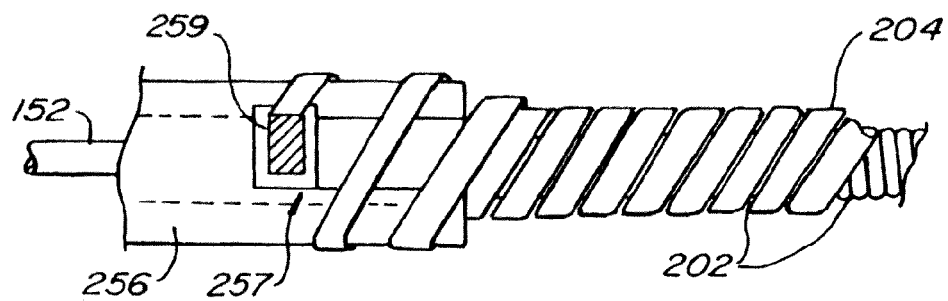
Figure 14G:
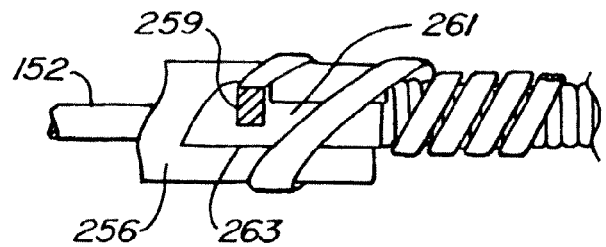
Figure 14H:
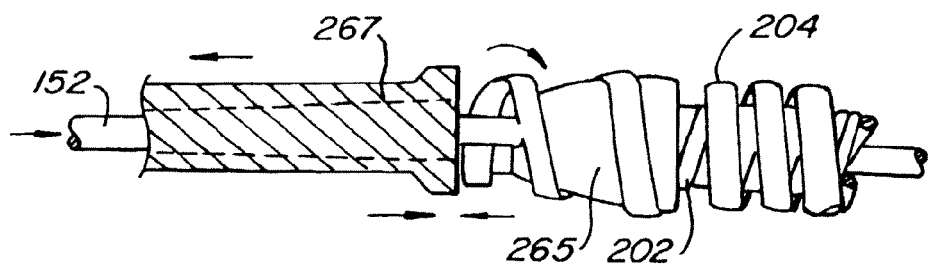

Alternative structures for releasably restraining secondary coil 204 are illustrated in FIGS. 14F-H. In the embodiments of FIGS. 14F and G, corewire 152 is rotationally coupled to primary coil 202, and hence to the distal portion of secondary coil 204 by bond 206 (see FIG. 14C). A tab 259 is affixed to a proximal end of secondary coil 204, the tab preferably protruding radially inwardly from the coil, the tab ideally comprising a small diameter annulus or collar having an axis parallel to the secondary coil axis. Tab 259 is releasably received by a keyhole slot 257 in delivery catheter 256. The tab is axially restrained in the slot when the tab engages one side of the slot, but is free to slide axially from the slot when rotationally disengaged or pressed against the other side.

Prior to delivery, secondary coil 204 is restrained in a small diameter configuration by engagement between tab 259 and slot 257. Secondary coil 204 is tightly wound down, so that the secondary coil biases the tab toward the restrained position. The proximal portions of the corewire and delivery catheter can be rotationally affixed to each other (ideally by a Tohey-Borst valve) to restrain the device in the small configuration. This may also prevent distal movement of the contraceptive device from the catheter and corewire.

Once the device is positioned, allowing the proximal portions of the corewire and catheter to rotate relative to each other (by releasing the Tohey-Borst valve or the like), and/or actively rotating one of these structures, can unwind the secondary coil and allow tab 259 to slide axially free of the catheter. Optionally, as shown in FIG. 14G, an alternative keyhole slot 263 having an angled or radiused proximal surface may be used to urge tab 259 toward a release portion 261 of the slot by pushing the surface distally against the tab.

Still further release mechanisms are possible, including the system illustrated in FIG. 14H. A proximally inwardly tapering body or brake 265 is affixed to primary coil 202, and is fittingly received by a tapering receptacle at the distal end of delivery catheter 267 when a proximal portion of secondary coil 204 is disposed therebetween. Secondary coil 204 may optionally be held in its wound-down configuration at the proximal end of the delivery system by a Tohey-Borst valve, and can be released to unwind by moving the catheter proximally relative to corewire 152 (and hence primary coil 202 and body 265), and/or by releasing the Tohey-Borst valve.

The use of a tubular, radially expandable intrafallopian device, and also the significance of tissue reaction in providing functional occlusion, can be further understood with reference to FIGS. 15A-D. A lumen L of a fallopian tube F is largely a potential space, much like a deflated balloon. Tubal wall W can expand around structures which are inserted into lumen L, such as around catheter 256 which radially restrains a free ended secondary coil 204. Hence, the size of the irregular lumenal cross-section may be measured by the diameter of a device it can accommodate.

Work in connection with the present invention has found that fallopian tubes can vary significantly in inner lumen cross-sectional sizes. The maximum diameter of a device which a fallopian tube can accommodate at its smallest point can range anywhere from 0.2 to 1.5 mm. For devices having a fixed cross-section, relatively large diameters will make the device more difficult to deliver. However, if the device is made too small, it can be more easily ejected from the fallopian tube. While fixed cross-sectional devices may still be effective (for example, by providing a range of different device sizes), the use of a radially expandable tubular structure such as free ended helical coil 204 allows the device to compensate for the substantially anatomical differences between users.

Figure 15A:
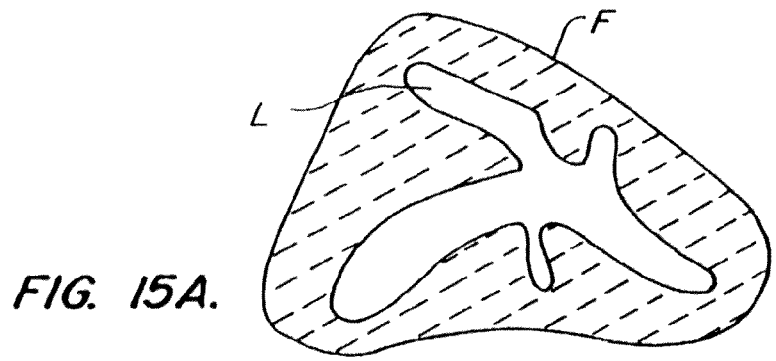
FIG. 15A-D illustrate cross-sectional views through the fallopian tube before, during, and after delivery of a contraceptive device having a radially expandable helical coil, and also illustrates the enhanced efficacy provided by tissue reactions such as tissue ingrowth into and around the helical coil.
Figure 15B:
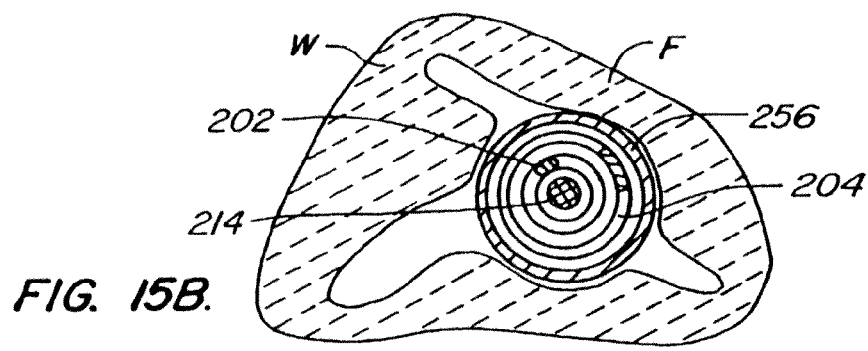
Figure 15C:
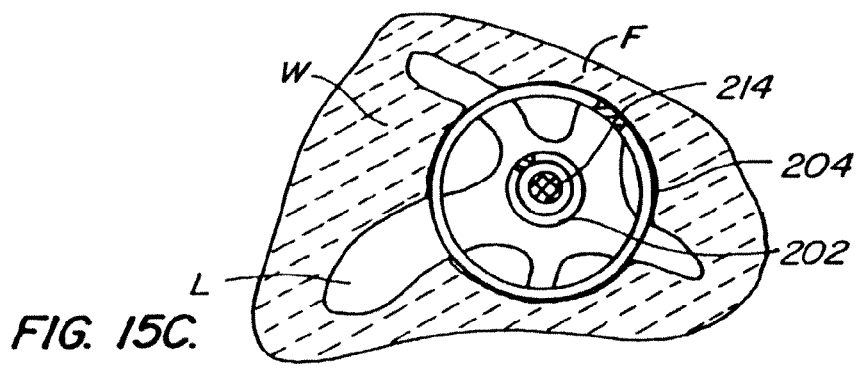

As generally described above, catheter 256 may optionally be positioned by first accessing the fallopian tube with a guidewire, and then advancing the catheter over the positioned guidewire. Alternatively, the catheter and contraceptive device may be advanced distally using the distal end of the primary coil as a guidewire. Regardless, once the contraceptive device is positioned at the desired axial location (generally from adjacent the isthmus to the intraluminal region, but optionally anywhere from the corneal area to adjacent the distal fimbria), catheter 256 is withdrawn proximally while restraining the contraceptive device axially with the proximal end of corewire 214. As catheter 256 is withdrawn, secondary coil 204 expands radially and engages the surrounding tubal wall W, as illustrated in FIG. 15C. Secondary coil 204 may optionally be torqued against the surrounding tubal wall from the proximal end of corewire 214, after which the corewire is unthreaded from the contraceptive device and removed.

Figure 15D:
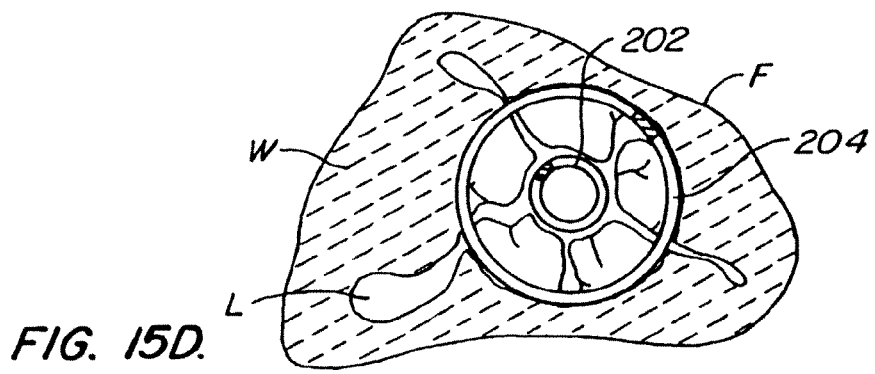

Although the tissues of the tubal wall protrude between the windings of secondary coil 204, a significant portion of lumen L remains open. Nonetheless, functional occlusion is provided so long as the deployed device adequately interferes with fertilization so as to inhibit conception. Functional occlusion may be enhanced by the formation of scar tissues and the growth of tissues from the tubal wall so as to occlude lumen L (ideally both inside and outside of the tubular retention structure), as illustrated in FIG. 15D. Such scar tissue formation will also aid in anchoring the device.

Figure 16:
FIG. 16 illustrates a contraceptive delivery system having a detachable distal corewire.

As can be understood with reference to FIG. 15D and FIG. 16, open areas within the contraceptive device along the axis of fallopian tube F can present some risk of providing a passageway for fertilization. To avoid providing a prosthetic lumen defined by the inner surface of primary coil 202 after corewire 214 is removed, a detachable delivery wire 260 is formed in two pieces. Distal delivery wire 264 is coupled to 10 proximal delivery wire 262 by a threaded fastener 266. Fastener 266 provides column strength to the detachable delivery wire. This allows the distal portion of the delivery wire to remain within the primary coil when the contraceptive device is detached. Clearly, a wide variety of coupling mechanisms might be used. Advantageously, a threaded coupler allows the device to be torqued in one direction and detached by rotating the proximal delivery wire 262 in the other direction, generally as described above.

Figure 15E:
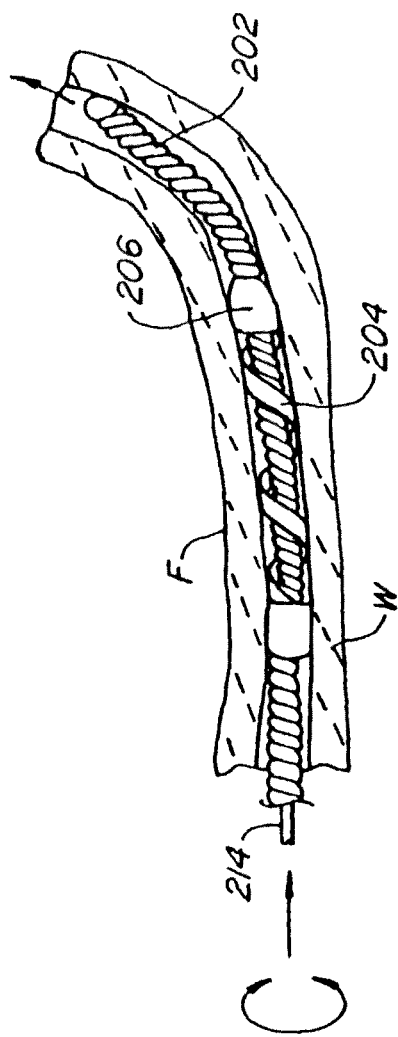
FIG. 15E illustrates the self-guiding capabilities of a contraceptive device having a straight primary coil.

The use of primary coil 202 (in combination with corewire 214) as a guidewire can be understood with reference to FIG. 15E. The good proximal column strength of the corewire and the distally increasing flexibility of the combined corewire and primary coil at the distal end of the delivery device greatly facilitates axially advancing the device within fallopian tube F. The ability of the corewire 214 to transmit torque can also help advance the delivery system distally, as well as allowing the user to embed secondary coil 204 into the surrounding tubal wall. As can also be understood with reference to FIG. 15E, the use of a straight primary coil in a portion of the fallopian tube having significant axial curvature results in resilient engagement of the coil against the tubal wall, and can thereby provide anchoring similar to that described above for pre-bent coils in straight lumens.

Figure 17:
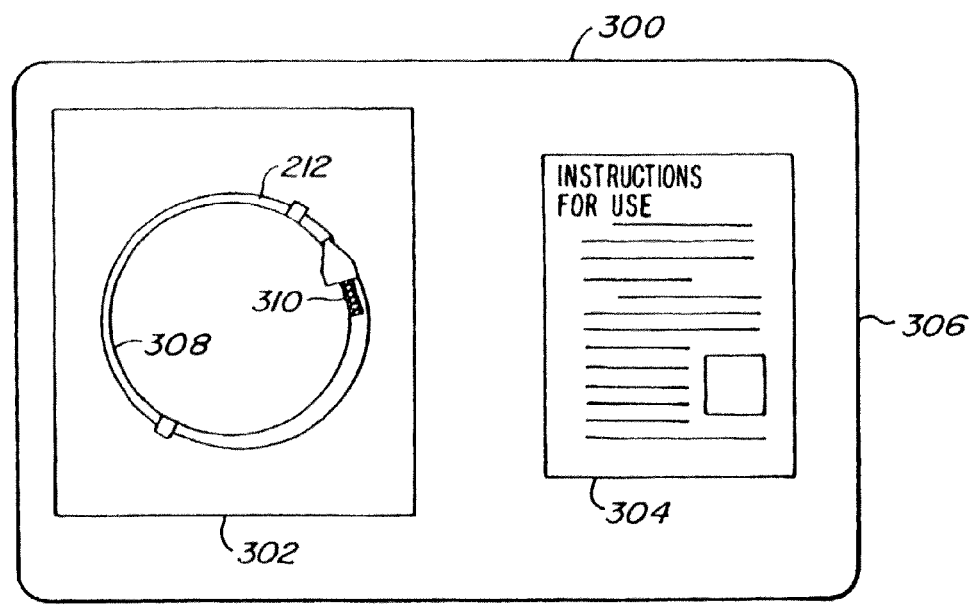
FIG. 17 schematically illustrates a kit including a contraceptive delivery system and instructions for its use.

Referring now to FIG. 17, a kit 300 includes contraceptive system 212 (in which straight contraceptive device 200 is mounted on corewire 214) within a sterile package 302. Also included in kit 300 are instructions 304, the sterile package and instructions being disposed in packaging 306. The instructions may set forth any of the method steps for using a contraceptive system as described hereinabove. Delivery system 212 may be protected by a protective sheath 308, and other system components described hereinabove may also be included. Also visible in FIG. 17 is the proximal torquable handle 310 of the delivery system.

Instructions 304 will often comprise printed material, and may be found in whole or in-part on packaging 306 or sterile packaging 302. Alternatively, instructions 304 may be in the form of a recording disk or other computer readable data, a video tape, a sound recording, or the like.

Figure 18A:
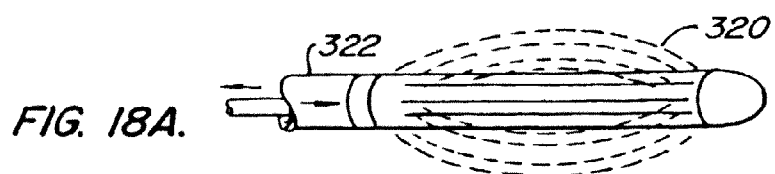
FIGS. 18A-C schematically illustrate alternative tubular radially expandable retention structures which can mechanically anchor a contraceptive device in the fallopian tube.
Figure 18B:
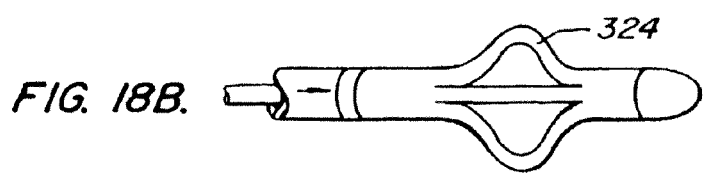
Figure 18C:
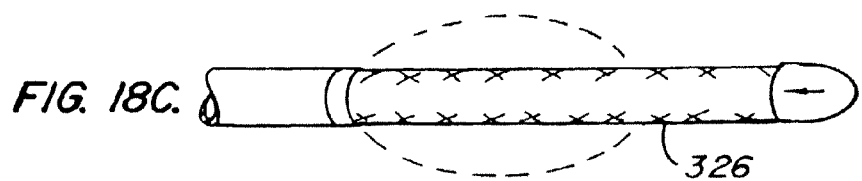

Alternative radially expandable retention structures are illustrated in FIGS. 18A through C. A slotted tube retention structure 320 can shorten and expand within the fallopian tube. In general, such expansion may be the result of external forces (such as actuation of a two part delivery system 322), or the retention structure may self-expand when released in situ. Forcibly expanded retention structures may have a latching mechanism which prevents collapse when the device is detached from the delivery system in the fallopian tube, and such detachment may be effected by any of the mechanisms described hereinabove.

Still further alternative retention structures may be used in place of helical secondary coil 204 and slotted tube 320. For example, a Malecott retention structure 324 or a braided filament retention structure 326 might be expanded to engage a surrounding tubal wall. In some cases, tubal anchoring may be enhanced by including two or more retention structures, or by providing small barbs which extend axially and/or radially from the expanded retention structure to prevent axial migration. Preferably, such barbs would be too short to perforate through the tubal wall. A wide variety of alternative radially expansible structures which might be adapted for use as a retaining structure in the present intrafallopian contraceptive device are described with reference to vascular stents.

Figure 19A:
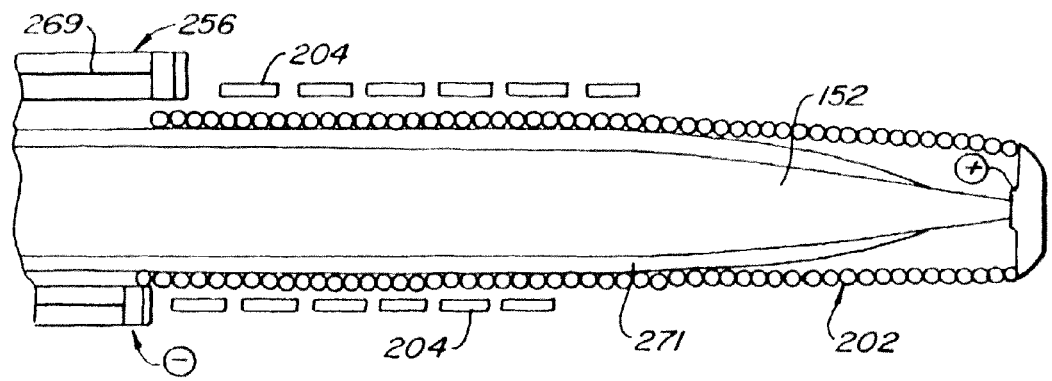
FIGS. 19A and B illustrate an intrafallopian contraceptive system in which a hand-held battery electrically actuates the retention structure by transmitting a current which heats a shape-memory alloy of the retention structure.
Figure 19B:
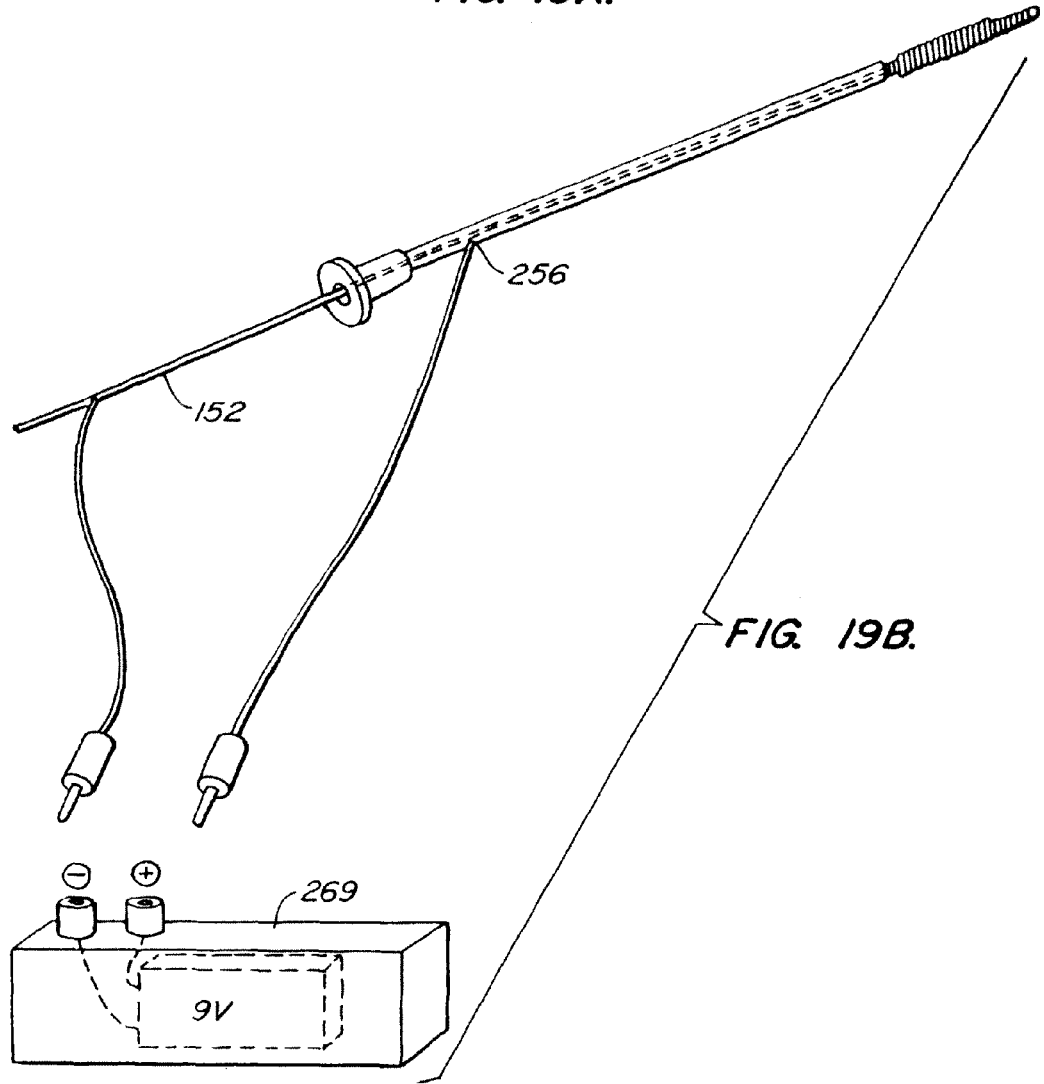

An intrafallopian device having a retaining structure comprising a shape memory alloy is illustrated in FIGS. 19A and B. In general, the system applies energy to the contraceptive device so that the device expands from a low profile (for delivery) to a deployed profile so as to hold the device in place. The device may be heated by transmitting Current along two electrically isolated conductors to primary coil 202. Corewire 152 here has an insulating layer 271 and is coupled to a first portion of the coil, while a conductor 269 in delivery catheter 256 is coupled to another portion of the coil. The resistance of the coil to a small current is sufficient to heat and reconfigure the retaining structure. Electrical energy from a common 9-volt hand-held battery within energy source will be sufficient to reconfigure secondary coil 204, which will generally remain in the deployed configuration at body temperature. Alternative energizing systems may use heated saline or the like.

Figure 20A:
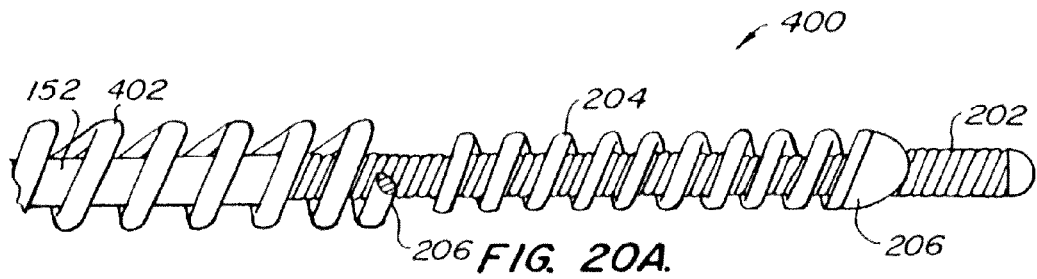
FIGS. 20A and B illustrate an intrafallopian contraceptive device and method for its use to support a coil comprising copper within the utero-tubal junction.
Figure 20B:
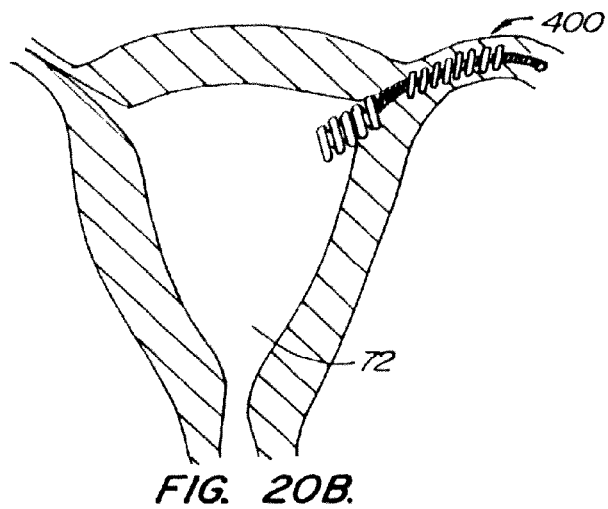
Figure 21A:
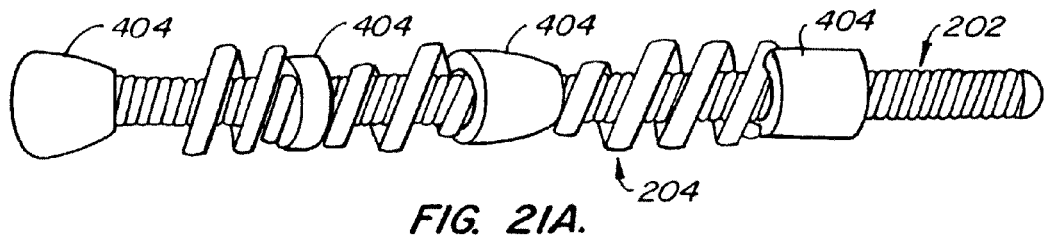
FIGS. 21A-C illustrate alternative structures comprising copper and methods for their use to inhibit conception, according to the principles of the present invention.
Figure 21B:
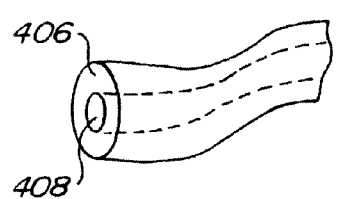
Figure 21C:
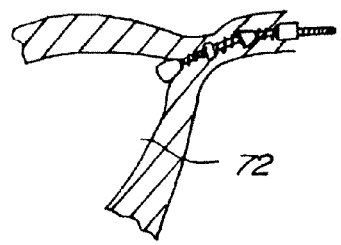

As described above, copper may enhance the efficacy of an intrafallopian contraceptive device 400. A1 illustrated in FIGS. 20A and B, a copper body (for example, in the form of copper coil 402) may extend proximally into and/or through the utero-tubal junction from the fallopian tube. As can be seen in FIGS. 21A and C, the copper may alternatively be in the form of copper beads 404, which may be used to form bonds, ingrowth structures, or the like. The copper may be in the form of a plating 406 over a core material 408 for use in the primary coil, secondary coil, or the like.

The release rate of copper is often closely related to the surface area of copper on the device. A total copper surface area over 100 mm2, and most often in a range from about 300 mm2 to about 400 mm2 will be preferred to provide contraception.

The total volume of copper will affect the duration of the enhanced efficacy the copper provides. To provide lifelong contraception, we should provide sufficient copper for about 25 years (based on the fertility life of a woman). For an exposed copper surface area of 400 mm2, average copper release rates may be about 25 micrograms per day, based on intrauterine device studies. To allow our intrafallopian contraceptive devices to release copper at this rate for 25 years, we will preferably include at least 0.23 grams or 25.6 mm3 of total copper. To provide a reasonable safety factor, a 25-year device may include at least about 0.34 grams or 38.4 mm2 of copper volume. These quantities may be provided by each device, or by two devices (in the left and right fallopian tubes) in combination. Similar calculations may be performed for year devices (using the same exposed area and at least ⅕ of the above volume), or to adjust for differing release/areal efficacy resulting from the copper structures being carried in different regions of the fallopian tubes.

In conclusion, the present invention provides a contraceptive intrafallopian device which may be positioned without surgery. While the above is a complete description of the preferred embodiments of the invention, various alternatives, modifications, and equivalents may be used. For example, a wide variety of secondary shapes, including open loops, continuous bends, sinusoidal curves, or the like, may be imposed on the primary coil. Additionally, aspects of these intrafallopian contraceptive devices which are described separately may often be combined (for example, a self-guiding device may also promote ingrowth to affix the device in the fallopian tube). Therefore, the above description should not be taken as limiting the scope of the invention, which is defined instead solely by the appended claims.

What is claimed is:

1. A contraceptive device comprising:
a resilient primary coil, when in a relaxed state, comprising:
   a proximal anchor of the primary coil bent into a proximal secondary loop having a proximal cross-section;
   a distal anchor of the primary coil bent into a distal secondary loop having a distal cross-section; and
   a lumen-traversing region of the primary coil extending between the proximal anchor and the distal anchor, the lumen traversing region of the primary coil having a cross-section which is smaller than both the proximal cross-section and the distal cross-section.

* * * * *